US007465741B2

(12) United States Patent
Andrés-Gil et al.

(10) Patent No.: US 7,465,741 B2
(45) Date of Patent: *Dec. 16, 2008

(54) C-SUBSTITUTED TRICYCLIC ISOXAZOLINE DERIVATIVES AND THEIR USE AS ANTI-DEPRESSANTS

(75) Inventors: José Ignacio Andrés-Gil, Madrid (ES); José Manuel Bartolomé-Nebreda, Toledo (ES); Rosa Maria Alvarez-Escobar, Toledo (ES); Margaretha Henrica Maria Bakker, Alsbach-Haehnlein (DE); Antonius Adrianus Hendrikus Petrus Megens, Beerse (BE)

(73) Assignee: Janssen Pharmaceutica N.V., Beerse (BG)

( * ) Notice: Subject to any disclaimer, the term of this patent is extended or adjusted under 35 U.S.C. 154(b) by 343 days.

This patent is subject to a terminal disclaimer.

(21) Appl. No.: 10/524,197

(22) PCT Filed: Aug. 12, 2003

(86) PCT No.: PCT/EP03/50374

§ 371 (c)(1),
(2), (4) Date: Feb. 10, 2005

(87) PCT Pub. No.: WO2004/016621

PCT Pub. Date: Feb. 26, 2004

(65) Prior Publication Data

US 2005/0256119 A1      Nov. 17, 2005

(30) Foreign Application Priority Data

Aug. 12, 2002    (EP)    ................................... 02078322

(51) Int. Cl.
*A61K 31/44*    (2006.01)
*C07D 401/00*    (2006.01)
*C07D 491/00*    (2006.01)
*C07D 498/00*    (2006.01)
*C07D 515/00*    (2006.01)
*C07D 513/00*    (2006.01)

(52) U.S. Cl. ........................ 514/291; 514/293; 544/360; 544/374; 546/83; 546/89

(58) Field of Classification Search .................. 514/291, 514/293; 544/360, 374; 546/83, 89
See application file for complete search history.

(56) References Cited

U.S. PATENT DOCUMENTS

| 7,169,786 B2 * | 1/2007 | Andres-Gil et al. .... 514/253.03 |
| 2005/0222125 A1 * | 10/2005 | Andres-Gil et al. .... 514/217.07 |
| 2006/0122167 A1 * | 6/2006 | Andres-Gil et al. .... 514/210.21 |

FOREIGN PATENT DOCUMENTS

EP    0885883 A1    12/1998

| WO | WO 95/07893 A1 | 3/1995 |
| WO | WO 97/25317 A1 | 7/1997 |
| WO | WO 02/066484 A1 | 8/2002 |
| WO | WO 03/082878 A1 | 10/2003 |

OTHER PUBLICATIONS

International Search Report for PCT/EP03/50374 dated Nov. 28, 2003.
Andres, J. Ignacio et al., "Synhesis of 3a,4-Dihydro-3H-[1]benzopyrano[4,3-c]isoxazoles, Displaying Combined 5-HT Uptake Inhibiting and α₂-Adrenoceptor Anagonistic Activities: A Novel Series of Potential Antidepressants," Bioorganic & Medicinal Chemistry Letter 13 (2003) 2719-2725.
Eichinger, Karl et al., "A Convenient Synthesis of 3-and 3,4-Substituted 4,5-Dihydroisoxazole-5-acetic Acids," Synthetic Communications, 27(16), 2733-2742 (1997).

\* cited by examiner

*Primary Examiner*—James Wilson
*Assistant Examiner*—Erich A Leeser
(74) *Attorney, Agent, or Firm*—Woodcock Washburn LLP

(57) ABSTRACT

The invention concerns substituted tricyclic isoxazoline derivatives according to Formula (I), the pharmaceutically acceptable acid or base addition salts thereof, the stereochemically isomeric forms thereof and the N-oxide form thereof, more in particular tricyclic dihydrobenzopyranoisoxazoline, dihydroquinolinoisoxazoline, dihydronaphthalenoisoxazoline and dihydrobenzothiopyranoisoxazoline derivatives substituted on the phenylpart of the tricyclic moiety with at least one radical that is attached to the phenyl radical by a carbon-carbon bond as well as processes for their preparation, pharmaceutical compositions comprising them and their use as a medicine, in particular for treating depression, anxiety, movement disorders, psychosis, Parkinson's disease and body weight disorders including anorexia nervosa and bulimia, wherin all variables are defined in claim 1. (I) The compounds have surprisingly been shown to have selective serotonine (5-HT) reuptake inhibitor activity in combination with additional α₂-adrenocptor antagonist activity and show a strong antidepressant and/or anxiolytic activity and/or antipsychotic and/or a body weight control activity without being sedative. Also, in view of their selective serotonine (5-HT) reuptake inhibitor as well as α₂-adrenoceptor antagonist activity, compounds according to the invention are also suitable for treatment and/or prophylaxis in diseases where either one of the activities alone or the combination of said activities may be of therapeutic use.

(1)

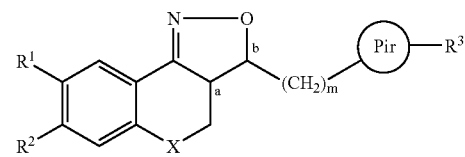

8 Claims, No Drawings

C-SUBSTITUTED TRICYCLIC ISOXAZOLINE DERIVATIVES AND THEIR USE AS ANTI-DEPRESSANTS

CROSS REFERENCE TO RELATED APPLICATIONS

This application is the national stage of Application No. PCT/EP03/50374, filed Aug. 12, 2003, which application claims priority from EP Patent Application No. 02078322.1 filed Aug. 12, 2002.

The invention concerns substituted tricyclic isoxazoline derivatives, more in particular tricyclic dihydrobenzopyranoisoxazoline, dihydroquinolinoisoxazoline, dihydronaphthalenoisoxazoline and dihydrobenzothiopyranoisoxazoline derivatives substituted on the phenylpart of the tricyclic moiety with at least one radical that is attached to the phenyl radical by a carbon-carbon bond as well as processes for their preparation, pharmaceutical compositions comprising them and their use as a medicine, in particular for treating depression, anxiety, movement disorders, psychosis, Parkinson's disease and body weight disorders including anorexia nervosa and bulimia.

The invention also relates to novel combination of said C-substituted tricyclic isoxazoline derivatives with antidepressants, anxiolytics, antipsychotics and anti-Parkinson's disease drugs.

Tetrahydronaphthalene and indane derivatives showing anti-depressant activity are known from EP-361 577 B1. These compounds are typical monoamine reuptake blockers with additional $\alpha_2$-adrenoceptor antagonist activity and they show anti-depressant activity without being sedative.

The problems associated with the compounds according to the state of the art is that the compounds cause considerable side-effects, such as nausea, excitation, an increased heart rate and a reduced sexual function. Furthermore, it requires a long time, in particular 3-4 weeks, before the response starts.

The purpose of the present invention is to provide novel compounds for treating depression, anxiety, movement disorders, psychosis, schizophrenia and body weight disorders, in particular compounds that do not exhibit the aforementioned disadvantages.

The present invention relates to novel substituted isoxazoline derivatives according to the general Formula (I)

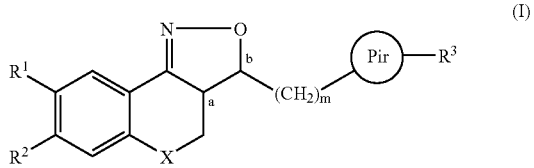

the pharmaceutically acceptable acid or base addition salts thereof, the stereochemically isomeric forms thereof and the N-oxide form thereof, wherein:

X is $CH_2$, N—$R^7$, S or O;

$R^7$ is selected from the group of hydrogen, alkyl, Ar, Ar-alkyl, alkylcarbonyl, alkyloxycarbonyl and mono- and di(alkyl)aminocarbonyl;

$R^1$ and $R^2$ are each selected from the group of hydrogen, halo, hydroxy, —$OSO_2H$, —$OSO_2CH_3$, alkyloxy, alkyloxyalkyloxy, alkyloxyalkyloxyalkyloxy, tetrahydrofuranyloxy, alkylcarbonyloxy, alkyloxyalkylcarbonyloxy, pyridinylcarbonyloxy, alkylcarbonyloxyalkyloxy, alkyloxycarbonyloxy, alkenyloxy, alkenylcarbonyloxy, mono- or di(alkyl)aminoalkyloxy, —N—$R^{10}R^{11}$, alkylthio, Alk, Ar and Het, with the proviso that at least one of $R^1$ and $R^2$ is selected from the group Alk, Ar or Het, wherein Alk is cyano, CN—OH, CN-oxyalkyl, alkyl, alkyloxyalkyl, alkyloxyalkyloxyalkyl, alkyloxyalkyloxyalkyloxyalkyl, alkylcarbonylalkyl, alkylcarbonyloxyalkyl, alkyloxycarbonylalkyl, Ar-alkyl, Ar-carbonylalkyl, Ar-oxyalkyl, mono- or di(alkyl)aminoalkyl, mono- or di(alkylcarbonyl)aminoalkyl, mono- or di(alkyl)aminocarbonyl-alkyl, Het-alkyl, formyl, alkylcarbonyl, alkyloxycarbonyl, alkyloxyalkyl-carbonyl, mono- or di(alkyl)aminocarbonyl, Ar-carbonyl and Ar-oxycarbonyl;

Ar is phenyl or naphthyl, optionally substituted with one or more halo, cyano, oxo, hydroxy, alkyl, formyl, alkyloxy or amino radicals.

Het is a heterocyclic radical selected from the group of $Het^1$, $Het^2$ and $Het^3$;

$Het^1$ is an aliphatic monocyclic heterocyclic radical selected from the group of pyrrolidinyl, dioxolyl, imidazolidinyl, pyrrazolidinyl, piperidinyl, dioxyl, morpholinyl, dithianyl, thiomorpholinyl, piperazinyl and tetrahydrofuryl;

$Het^2$ is a semi-aromatic monocyclic heterocyclic radical selected from the group of 2H-pyrrolyl, pyrrolinyl, imidazolinyl and pyrrazolinyl, $Het^3$ is an aromatic monocyclic heterocyclic radical selected from the group of pyrrolyl, pyrazolyl, imidazolyl, furyl, thienyl, oxazolyl, isoxazolyl, thiazolyl, isothiazolyl, pyridinyl, pyrimidinyl, pyrazinyl, pyridazinyl and triazinyl; or an aromatic bicyclic heterocyclic radical selected from the group of quinolinyl, quinoxalinyl, indolyl, benzimidazolyl, benzoxazolyl, benzisoxazolyl, benzothiazolyl, benzisothiazolyl, benzofuranyl and benzothienyl;

wherein each $Het^1$, $Het^2$ and $Het^3$-radical may optionally be substituted on either a carbon or heteroatom with halo, hydroxy, alkyloxy, alkyl, Ar, Ar-alkyl, formyl, alkylcarbonyl or pyridinyl;

$R^{10}$ and $R^{11}$ are each, independently from each other, selected from the group of hydrogen, alkyl, Ar, Ar-alkyl, pyrrolidinylalkyl, piperidinylalkyl, homopiperidinylalkyl, piperazinylalkyl, morpholinylalkyl, mono- or di(alkyl)aminoalkyl, alkylcarbonyl, alkenylcarbonyl, Ar-carbonyl, pyridinylcarbonyl, alkyloxycarbonyl, mono- or di(alkyl)aminocarbonyl, mono- or di(Ar)aminocarbonyl, mono- or di(alkyloxycarbonylalkyl)-aminocarbonyl, pyrrolidinylcarbonyl, aminoiminomethyl, alkylaminoiminomethyl, N-benzylpiperazinyliminomethyl, alkylsulphonyl and Ar-sulphonyl; or $R^{10}$ and $R^{11}$ may be taken together and with the N may form a monovalent radical selected from the group of

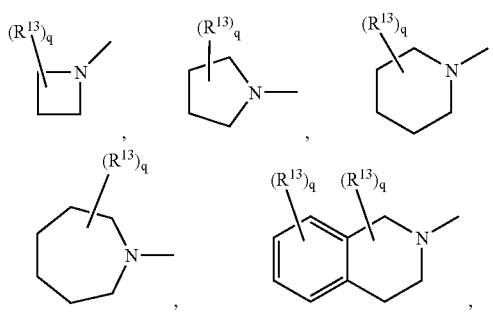

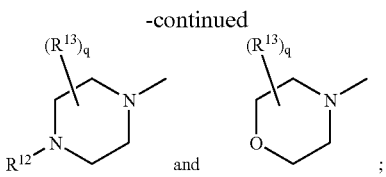

wherein:
$R^{12}$ is selected from the group of hydrogen, alkyl, Ar, Ar-alkyl, Ar-alkenyl, alkylcarbonyl, alkyloxycarbonyl, alkyloxyalkylcarbonyl and mono- or di(alkyl)aminocarbonyl;

each ring being optionally substituted with q radicals $R^{13}$, each radical independently from each other selected from the group of alkyl, oxo, Ar, Ar-alkyl, Ar-alkenyl and alkyloxycarbonyl and q being an integer ranging from 0 to 6; or $R^1$ and $R^2$ may be taken together to form a bivalent radical —$R^1$—$R^2$— selected from the group of —CH$_2$—CH$_2$—CH$_2$—CH$_2$—, —CH=CH—CH$_2$—CH$_2$—, —CH$_2$—CH$_2$—CH=CH—, —CH$_2$—CH=CH—CH$_2$— and —CH=CH—CH=CH—;

a and b are asymmetric centers;

(CH$_2$)$_m$ is a straight hydrocarbon chain of m carbon atoms, m being an integer ranging from 1 to 4;

Pir is a radical according to any one of Formula (IIa), (IIb) or (IIc)

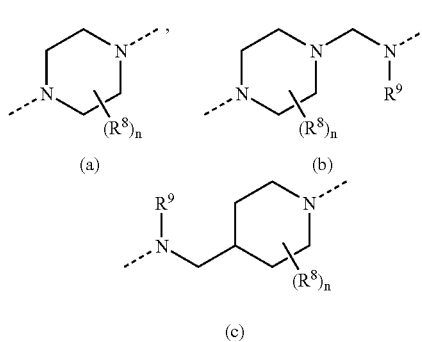

optionally substituted with n radicals $R^8$, wherein:
each $R^8$ is independently from each other, selected from the group of hydroxy, amino, nitro, cyano, halo and alkyl;
n is an integer ranging from 0 to 5;
$R^9$ is selected from the group of hydrogen, alkyl and formyl;

$R^3$ represents an optionally substituted aromatic homocyclic or heterocyclic ring system together with an optionally substituted and partially or completely hydrogenated hydrocarbon chain of 1 to 6 atoms long with which said ring system is attached to the Pir radical and of which may contain one or more heteroatoms selected from the group of O, N and S;

alkyl represents a straight or branched saturated hydrocarbon radical having from 1 to 6 carbon atoms or a cyclic saturated hydrocarbon radical having from 3 to 6 carbon atoms, optionally substituted with one or more halo, cyano, oxo, hydroxy, formyl or amino radicals and alkenyl represents a straight or branched unsaturated hydrocarbon radical having one or more double bonds, optionally substituted with one or more halo, cyano, oxo, hydroxy, formyl or amino radicals;

More in particular, the invention relates to compounds according to Formula (I), the pharmaceutically acceptable acid or base addition salts thereof, the stereochemically isomeric forms thereof and the N-oxide form thereof, wherein $R^3$ is a radical according to any one of Formula (IIIa), (IIIb) or (IIIc)

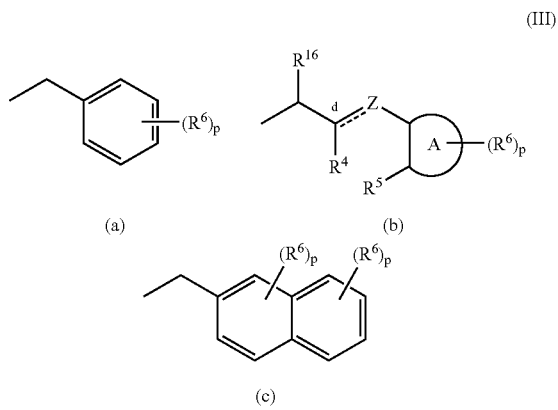

wherein:
d is a single bond while Z is a bivalent radical selected from the group of —CH$_2$—, —C(=O)—, —CH(OH)—, —C(=N—OH)—, —CH(alkyl)-, —O—, —S—, —S(=O)—, —NH— and —SH—; or d is a double bond while Z is a tlivalent radical of formula =CH— or =C(alkyl)-;

A is a 5- or 6-membered aromatic homocyclic or heterocyclic ring, selected from the group of phenyl, pyranyl, pyridinyl, pyrazinyl, pyrimidinyl, pyridazinyl, thienyl, isothiazolyl, pyrrolyl, imidazolyl, pyrazolyl, furanyl, oxadiazolyl and isoxazolyl;

p is an integer ranging from 0 to 6;

$R^4$ and $R^5$ are each, independently from each other, selected from the group of hydrogen, alkyl, Ar, biphenyl, halo and cyano; or $R^4$ and $R^5$ may be taken together to form a bivalent radical —$R^4$—$R^5$— selected from the group of —CH$_2$—, =CH—, —CH$_2$—CH$_2$—, —CH=CH—, —O—, —NH—, =N—, —S—, —CH$_2$N(-alkyl)-, —N(-alkyl)CH$_2$—, —CH$_2$NH—, —NHCH$_2$—, —CH—N—, —N=CH—, —CH$_2$O— and —OCH$_2$—;

each $R^6$ is independently from each other, selected from the group of hydroxy, amino, nitro, cyano, halo, carboxyl, alkyl, Ar, alkyloxy, Ar-oxy, alkyl-carbonyloxy, alkyloxycarbonyl, alkylthio, mono- and di(alkyl)amino, alkylcarbonylamino, mono- and di(alkyl)aminocarbonyl, mono- and di(alkyl)aminocarbonyloxy, mono- and di(alkyl)aminoalkyloxy; or two vicinal radicals $R^6$ may be taken together to form a bivalent radical —$R^6$—$R^6$— selected from the group of —CH$_2$—CH$_2$—O—, —O—CH$_2$—CH$_2$—, —O—CH$_2$—C(=O)—, —C(=O)—CH$_2$—O—, —O—CH$_2$—O—, —CH$_2$—O—CH$_2$—, —O—CH$_2$—CH$_2$—O—, —CH=CH—CH=CH—, —CH=CH—CH=N—, —CH=CH—N=CH—, —CH=N—CH=CH—, —N=CH—CH=CH—, —CH$_2$—CH$_2$—CH$_2$—, —CH$_2$—CH$_2$—C(=O)—, —C(=O)—CH$_2$—CH$_2$—, —CH$_2$—C(=O)—CH$_2$— and —CH$_2$—CH$_2$—CH$_2$—CH$_2$— and R$^{16}$ is selected from the group of hydrogen, alkyl, Ar and Ar-alkyl.

Preferably, the invention relates to those compounds according to Formula (I), the pharmaceutically acceptable acid or base addition salts thereof, the stereochemically isomeric forms thereof and the N-oxide form thereof, wherein X=O; m=1; Pir is a radical according to Formula (IIa) wherein n=0; R$^3$ is a radical according to Formula (IIIb) wherein d is a double bond while Z is a trivalent radical of formula =H—, A is a phenyl ring, R$^4$ is hydrogen or alkyl, R$^5$ and R$^{16}$ are each hydrogen, R$^6$ is hydrogen or halo and p=1.

More preferably, the invention relates to compounds according to Formula (I), the pharmaceutically acceptable acid or base addition salts thereof, the stereochemically isomeric forms thereof and the N-oxide form thereof, wherein at least one of R$^1$ and R$^2$ is selected from the group of cyano optionally substituted with hydroxy or alkyloxy; alkyl; hydroxyalkyl; aminoalkyl; alkyloxyalkyl; alkyloxyalkyloxyalkyloxyalkyl; alkylcarbonyloxyalkyl; Ar-oxyalkyl; mono- or di(alkyl)aminoalkyl, the alkyl radicals optionally substituted with hydroxy; mono- or di(alkylcarbonyl)aminoalkyl; mono- or di(alkyl)aminocarbonyl; piperidinylalkyl; morpholinylalkyl; phenyl and thienyl optionally substituted with alkylcarbonyl.

Most preferably, the invention relates to compounds with the following names:

8-Methyl-3-[4-(3-phenyl-allyl)-piperazin-1-ylmethyl]-3a,4-dihydro-3H-chromeno[4,3-c]isoxazole;

8-Methoxy-7-methyl-3-[4-(2-methyl-3-phenyl-allyl)-piperazin-1-ylmethyl]-3a,4-dihydro-3H-chromeno[4,3-c]isoxazole;

{8-Methoxy-3-[4-(2-methyl-3-phenyl-allyl)-piperazin-1-ylmethyl]-3a,4-dihydro-3H-chromeno[4,3-c]isoxazol-7-yl}-methanol;

7-Methoxymethyl-3-[4-(2-methyl-3-phenyl-allyl)-piperazin-1-ylmethyl]-3a,4-dihydro-3H-chromeno[4,3-c]isoxazole;

8-Methoxy-7-(2-methoxy-ethoxymethoxymethyl)-3-[4-(2-methyl-3-phenyl-allyl)-piperazin-1-ylmethyl]-3a,4-dihydro-3H-chromeno[4,3-c]isoxazole;

Acetic acid 8-methoxy-3-[4-(2-methyl-3-phenyl-allyl)-piperazin-1-ylmethyl]-3a,4-dihydro-3H-chromeno[4,3-c]isoxazol-7-ylmethyl ester;

8-Methoxy-3-[4-(2-methyl-3-phenyl-allyl)-piperazin-1-ylmethyl]-7-phenoxymethyl-3a,4-dihydro-3H-chromeno[4,3-c]isoxazole;

2-(Methyl-{3-[4-(2-methyl-3-phenyl-allyl)-piperazin-1-ylmethyl]-3a,4-dihydro-3H-chromeno[4,3-c]isoxazol-7-ylmethyl}-amino)-ethanol;

8-Methoxy-3-[4-(2-methyl-3-phenyl-allyl)-piperazin-1-ylmethyl]-7-morpholin-4-ylmethyl-3a,4-dihydro-3H-chromeno[4,3-c]isoxazole;

3-[4-(2-Methyl-3-phenyl-allyl)-piperazin-1-ylmethyl]-3a,4-dihydro-3H-chromeno[4,3-c]isoxazole-7-carbaldehyde oxime;

3-[4-(2-Methyl-3-phenyl-allyl)-piperazin-1-ylmethyl]-3a,4-dihydro-3H-chromeno[4,3-c]isoxazole-7-carbaldehyde O-methyl-oxime;

3-[4-(2-Methyl-3-phenyl-allyl)-piperazin-1-ylmethyl]-3a,4-dihydro-3H-chromeno[4,3-c]isoxazole-7-carbonitrile;

N-{3-[4-(2-Methyl-3-phenyl-allyl)-piperazin-1-ylmethyl]-3a,4-dihydro-3H-chromeno[4,3-c]isoxazol-7-ylmethyl}-acetamide;

8-Methoxy-3-[4-(2-methyl-3-phenyl-allyl)-piperazin-1-ylmethyl]-3a,4-dihydro-3H-chromeno[4,3-c]isoxazole-7-carboxylic acid ethylamide;

8-Methoxy-3-[4-(2-methyl-3-phenyl-allyl)-piperazin-1-ylmethyl]-7-phenyl-3a,4-dihydro-3H-chromeno[4,3-c]isoxazole;

1-(5-{8-Methoxy-3-[4-(2-methyl-3-phenyl-allyl)-piperazin-1-ylmethyl]-3a,4-dihydro-3H-chromeno[4,3-c]isoxazol-7-yl}-thiophen-2-yl)-ethanone.

In the framework of this application, alkyl defines straight or branched saturated hydrocarbon radicals having from 1 to 6 carbon atoms, for example methyl, ethyl, propyl, butyl, 1-methylpropyl, 1,1-dimethylethyl, pentyl, hexyl; or alkyl defines cyclic saturated hydrocarbon radicals having from 3 to 6 carbon atoms, for example cyclopropyl, methylcyclopropyl, cyclobutyl, cyclopentyl and cyclohexyl. Alkyl radicals may be optionally substituted with one or more halo, cyano, oxo, hydroxy, formyl or amino radicals, for example polyhaloalkyl, in particular difluoromethyl and trifluoromethyl.

In the framework of this application, halo is generic to fluoro, chloro, bromo and iodo.

In the framework of this application, alkenyl represents a straight or branched unsaturated hydrocarbon radical having one or more double bonds, for example ethenyl, 1-propenyl, 2-propenyl and 1,3-butanedienyl. Alkenyl radicals may be optionally substituted with one or more halo, cyano, oxo, hydroxy, formyl or amino radicals, for example hydroxyethenyl.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to Formula (I) containing acidic protons may also be converted into their therapeutically active non-toxic metal or amine addition salts forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate base or acid.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds according to Formula (I) wherein one or several nitrogen atoms are oxidized to the so-called N-oxide, particularly those N-oxides wherein one or more nitrogens of the piperazinyl radical are N-oxidized.

The term "stereochemically isomeric forms" as used hereinbefore defines all the possible isomeric forms that the compounds according to Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds according to Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

Compounds according to Formula (I) and some of the intermediate compounds have at least two stereogenic centers in their structure, respectively denoted a and b in Formula (I). Due to the synthetic pathway followed for the synthesis of the tricyclic system, the configuration of those two asymmetric centers a and b is predetermined, so that the relative configuration of center a is S* and of center b is R*.

The invention also comprises derivative compounds (usually called "prodrugs") of the pharmacologically-active compounds according to the invention, which are degraded in vivo to yield the compounds according to the invention. Prodrugs are usually (but not always) of lower potency at the target receptor than the compounds to which they are degraded. Prodrugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on prodrugs may be found in Stella, V. J. et al., "Prodrugs", *Drug Delivery Systems,* 1985, pp. 112-176, and *Drugs,* 1985, 29, pp. 455-473.

Prodrugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the formula —COOR$^x$, where R$^x$ is a C$_{1-6}$alkyl, phenyl, benzyl or one of the following groups:

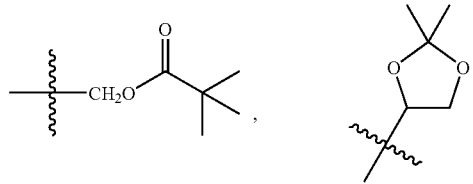

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

The compounds according to Formula (I) as prepared in the processes described below may be synthesized in the form of racemic mixtures of enantiomers that can be separated from one another following art-known resolution procedures. The racemic compounds according to Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds according to Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The compounds according to the invention, in particular compounds according to Formula (I), the pharmaceutically acceptable acid or base addition salts thereof, the stereochemically isomeric forms thereof and the N-oxide form thereof, have surprisingly been shown to have selective serotonine (5-HT) reuptake inhibitor activity in combination with additional α$_2$-adrenoceptor antagonist activity and show a strong anti-depressant and/or anxiolytic activity and/or antipsychotic and/or a body weight control activity without being sedative. Also, in view of their selective serotonine (5-HT) reuptake inhibitor as well as α$_2$-adrenoceptor antagonist activity, compounds according to the invention are also suitable for treatment and/or prophylaxis in diseases where either one of the activities alone or the combination of said activities may be of therapeutic use. In particular, the compounds according to the invention may be suitable for treatment and/or prophylaxis in the following diseases:

Central nervous system disorders, including:
 Mood disorders, including particularly major depressive disorder, depression with or without psychotic features, catatonic features, melancholic features, atypical features of postpartum onset and, in the case of recurrent episodes, with or without seasonal pattern, dysthymic disorder, bipolar I disorder, bipolar II disorder, cyclothymic disorder, recurrent brief depressive disorder, mixed affective disorder, bipolar disorder not otherwise specified, mood disorder due to a general medical condition, substance-induced mood disorder, mood disorder not otherwise specified, seasonal affective disorder and premenstrual dysphoric disorders.

Anxiety disorders, including panic attack, agoraphobia, panic disorder without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

Stress-related disorders associated with depression and/or anxiety, including acute stress reaction, adjustment disorders (brief depressive reaction, prolonged depressive reaction, mixed anxiety and depressive reaction, adjustment disorder with predominant disturbance of other emotions, adjustment disorder with predominant disturbance of conduct, adjustment disorder with mixed disturbance of emotions and conduct, adjustment disorders with other specified predominant symptoms) and other reactions to severe stress.

Dementia, amnesic disorders and cognitive disorders not otherwise specified, especially dementia caused by degenerative disorders, lesions, trauma, infections, vascular disorders, toxins, anoxia, vitamin deficiency or endocrinic disorders, or amnesic disorders caused by alcohol or other causes of thiamin deficiency, bilateral temporal lobe damage due to Herpes simplex encephalitis and other limbic encephalitis, neuronal loss secondary to anoxia/hypoglycemia/severe convulsions and surgery, degenerative disorders, vascular disorders or pathology around ventricle III.

Cognitive disorders due to cognitive impairment resulting from other medical conditions.

Personality disorders, including paranoid personality disorder, schizoid personality disorder, schizotypical personality disorder, antisocial personality disorder, borderline personality disorder, histrionic personality disorder, narcissistic personality disorder, avoidant personality disorder, dependent personality disorder, obsessive-compulsive personality disorder and personality disorder not otherwise specified.

Schizoaffective disorders resulting from various causes, including schizoaffective disorders of the manic type, of the depressive type, of mixed type, paranoid, disorganized, catatonic, undifferentiated and residual schizophrenia, schizophreniform disorder, schizoaffective disorder, delusional disorder, brief psychotic disorder, shared psychotic disorder, substance-induced psychotic disorder and psychotic disorder not otherwise specified.

Akinesia, akinetic-rigid syndromes, dyskinesia and medication-induced parkinsonism, Gilles de la Tourette syndrome and its symptoms, tremor, chorea, myoclonus, tics and dystonia.

Attention-deficit/hyperactivity disorder (ADHD).

Parkinson's disease, drug-induced Parkinsonism, post-encephalitic Parkinsonism, progressive supranuclear palsy, multiple system atrophy, corticobasal degeneration, parkinsonism-ALS dementia complex and basal ganglia calcification.

Dementia of the Alzheimer's type, with early or late onset, with depressed mood.

Behavioral disturbances and conduct disorders in dementia and the mentally retarded, including restlessness and agitation.

Extra-pyramidal movement disorders.

Down's syndrome.

Akathisia.

Eating Disorders, including anorexia nervosa, atypical anorexia nervosa, bulimia nervosa, atypical bulimia nervosa, overeating associated with other psychological disturbances, vomiting associated with other psychological disturbances and non-specified eating disorders.

AIDS-associated dementia.

Chronic pain conditions, including neuropathic pain, inflammatory pain, cancer pain and post-operative pain following surgery, including dental surgery. These indications might also include acute pain, skeletal muscle pain, low back pain, upper extremity pain, fibromyalgia and myofascial pain syndromes, orofascial pain, abdominal pain, phantom pain, tic douloureux and atypical face pain, nerve root damage and arachnoiditis, geriatric pain, central pain and inflammatory pain.

Neurodegenerative diseases, including Alzheimer's disease, Huntington's chorea, Creutzfeld-Jacob disease, Pick's disease, demyelinating disorders, such as multiple sclerosis and ALS, other neuropathies and neuralgia, multiple sclerosis, amyotropical lateral sclerosis, stroke and head trauma.

Addiction disorders, including:
  Substance dependence or abuse with or without physiological dependence, particularly where the substance is alcohol, amphetamines, amphetamine-like substances, caffeine, cannabis, cocaine, hallucinogens, inhalants, nicotine, opioids, phencyclidine, phencyclidine-like compounds, sedative-hypnotics, benzodiazepines and/or other substances, particularly useful for treating withdrawal from the above substances and alcohol withdrawal delirium.
  Mood disorders induced particularly by alcohol, amphetamines, caffeine, cannabis, cocaine, hallucinogens, inhalants, nicotine, opioids, phencyclidine, sedatives, hypnotics, anxiolitics and other substances.
  Anxiety disorders induced particularly by alcohol, amphetamines, caffeine, cannabis, cocaine, hallucinogens, inhalants, nicotine, opioids, phencyclidine, sedatives, hypnotics, anxiolitics and other substances and adjustment disorders with anxiety.

Smoking cessation.

Body weight control, including obesity.

Sleep disorders and disturbances, including
  Dyssomnias and/or parasomnias as primary sleep disorders, sleep disorders related to another mental disorder, sleep disorder due to a general medical condition and substance-induced sleep disorder.
  Circadian rhythms disorders.
  Improving the quality of sleep.

Sexual dysfunction, including sexual desire disorders, sexual arousal disorders, orgasmic disorders, sexual pain disorders, sexual dysfunction due to a general medical condition, substance-induced sexual dysfunction and sexual dysfunction not otherwise specified.

The present invention thus also relates to compounds according to Formula (I), the pharmaceutically acceptable acid or base addition salts thereof, the stereochemically isomeric forms thereof, the N-oxide form thereof, as well as the prodrugs thereof for use as a medicine, in particular for the treatment and/or prophylaxis of depression, anxiety, movement disorders, psychosis, Parkinson's disease and body weight disorders.

The present invention also relates to a method for the treatment and/or prophylaxis of diseases where either one of the activities (selective serotonine (5-HT) reuptake inhibitor and $\alpha_2$-adrenoceptor antagonist activity) alone or the combination of said activities may be of therapeutic use, in particular for the treatment and/or prophylaxis of depression, anxiety, movement disorders, psychosis, Parkinson's disease and body weight disorders comprising administering to a human in need of such administration an affective amount of a compound according to the invention, in particular according to Formula (I), the pharmaceutically acceptable acid or base addition salts thereof, the stereochemically isomeric forms thereof, the N-oxide form thereof, as well as the pro-drugs thereof.

The invention also relates to a pharmaceutical composition comprising a pharmaceutically acceptable carrier and, as active ingredient, a therapeutically effective amount of a compound according to the invention, in particular a compound according to Formula (I), the pharmaceutically acceptable acid or base addition salts thereof, the stereochemically isomeric forms thereof and the N-oxide form thereof or a prodrug as defined above.

The compounds according to the invention, in particular the compounds according to Formula (I), the pharmaceutically acceptable acid or base addition salts thereof, the stereochemically isomeric forms thereof and the N-oxide form thereof and the prodrugs, or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The compounds according to the invention may also be suitable as add-on treatment and/or prophylaxis in the above listed diseases in combination with any combination of compounds selected from the group of antidepressants, anxiolytics, antipsychotics and/or anti-Parkinson's disease drugs which are currently available or in development or which will become available in the future, to improve efficacy and/or onset of action. This is evaluated in rodent models in which antidepressants, anxiolytics, antipsychotics and/or anti-Parkinson's disease drugs are shown to be active. For example, compounds are evaluated in combination with antidepressants, anxiolytics, antipsychotics and/or anti-Parkinson's disease drugs for attenuation of stress-induced hyperthermia.

The invention therefore also relates to a pharmaceutical composition comprising the compounds according to the invention, in particular the compounds according to Formula (I), the pharmaceutically acceptable acid or base addition salts thereof, the stereochemically isomeric forms thereof and the N-oxide form thereof, and the prodrugs and one or more other compounds selected from the group of antidepressants, anxiolytics, antipsychotics and anti-Parkinson's disease drugs.

The invention also relates to the use of a pharmaceutical composition according to the invention for the manufacture of a medicament to improve efficacy and/or onset of action in the treatment and/or prophylaxis of depression, anxiety, movement disorders, psychosis, Parkinson's disease and body weight disorders.

Further, the invention relates to the use of a compound according to the invention for the manufacture of a medicament for the treatment and/or prophylaxis of depression, anxiety, movement disorders, psychosis, Parkinson's disease and body weight disorders, said treatment comprising the simultaneous or sequential administration of a compound according to the invention and one or more other compounds selected from the group of antidepressants, anxiolytics, anti-psychosis and anti-Parkinson's drugs.

The invention also relates to the use of one or more compounds selected from the group of antidepressants, anxiolytics and antipsychotics for the manufacture of a medicament for the treatment and/or prophylaxis of depression, anxiety and body weight disorders, said treatment comprising the simultaneous or sequential administration of one or more compounds selected from the group of antidepressants, anxiolytics and antipsychotics and anti-Parkinson's disease drugs and a compound according to any one of claims 1-7.

The invention further relates to a process for making a pharmaceutical composition comprising mixing a compound according to the invention, in particular the compounds according to Formula (I), the pharmaceutically acceptable acid or base addition salts thereof, the stereochemically isomeric forms thereof and the N-oxide form thereof, and the prodrugs, or any subgroup thereof and a compound selected from the group of antidepressants, anxiolytics, antipsychotics and anti-Parkinson's disease drugs and a pharmaceutically acceptable carrier.

In vitro receptor and neurotransmitter transporter binding and signal-transduction studies can be used to evaluate the $\alpha_2$-adrenoceptor antagonism activity and serotonine (5-HT) reuptake inhibitor activity of the present compounds. As indices for central penetration and potency to block the $\alpha_2$-adrenoceptors and serotonin transporters, respectively, ex vivo $\alpha_2$-adrenoceptor and serotonin transporter occupancy can be used. As indices of $\alpha_2$-adrenoceptor antagonism in vivo, the reversal of the loss of righting reflex, observed in rats after subcutaneous injection or oral dosage of the compound before intravenous medetomidine administration in rats can be used (medetomidine-test). As indices of serotonine (5-HT) reuptake inhibition activity, the inhibition of bead-twitches and excitation in rats, observed after subcutaneous injection or oral dosage of the compound before subcutaneous p-chloroamphetamine administration in rats can be used (pCA-test).

The compounds according to the invention can generally be prepared by a succession of steps, each of which is known to the skilled person.

In particular, the compounds according to Formula (I) can be prepared by a reaction (generally called a nucleophilic aromatic substitution reaction) with an intermediate compound according to Formula (V) on an intermediate compound according to Formula (IV),

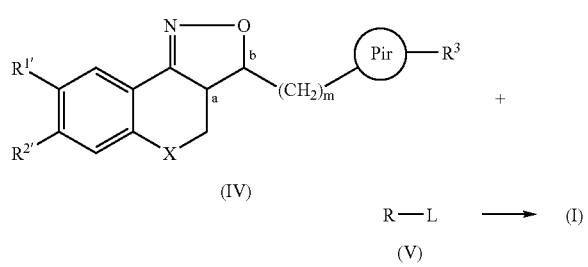

wherein all variables have the same meaning as in Formula (I), R is $R^1$ or $R^2$, L is a suitable leaving group, $R^{1'}$ and $R^{2'}$ are respectively equal to $R^1$ and $R^2$ with the proviso that at least one of $R^{1'}$ and $R^{2'}$ is an halogen. Such a reaction can also be formulated either as

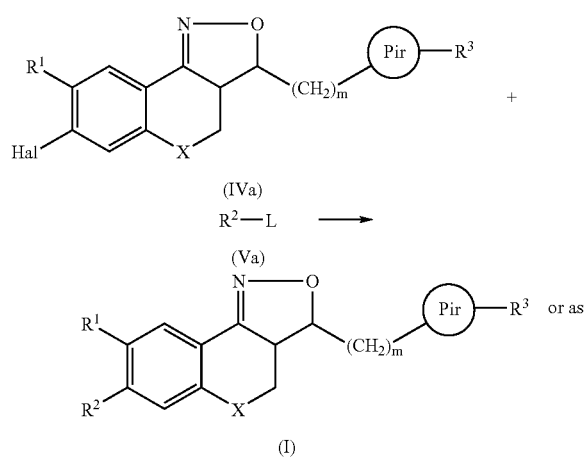

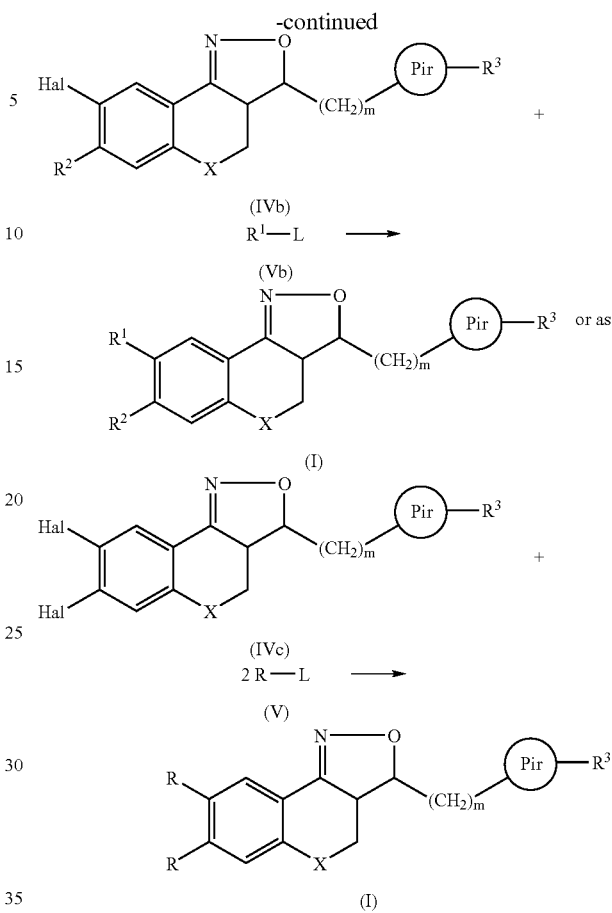

wherein R may be either $R^1$ or $R^2$ or both, Hal is a halogen atom such as chloro, bromo or iodo and L represents any suitable reactive leaving group, in particular halo, such as chloro, bromo or iodo, amino or a sulfonyloxy, such as methyl sulphonyloxy or 4-methylbenzenesulfonyloxy.

The above reactions are particular suitable for introducing an alkyl radical using e.g. an alkylhalide (Scheme 1, reaction (a)) or introducing a formyl radical using N,N'-dimethylformamide (Scheme 1, reaction (b)). Said reactions may be carried out in the presence of an alkyl-lithium derivative, such as n-butyllithium, under an inert atmosphere and in a dry solvent, such as tetrahydrofuran, at low temperatures ranging between −78° C. and 0° C. yielding the final compound according to Formula (I).

To introduce a phenyl radical (Scheme 1, reaction (m)), a Suzuki-type coupling reaction may be used by reaction of a boronic acid on a compound according to Formula (IVa) in the presence of a palladium catalyst such as Pd(PPh$_3$)$_4$ or Pd$_2$(dba)$_3$, a base, for example K$_2$CO$_3$, Na$_2$CO$_3$, CsCO$_3$ or potassium tert-butoxide, a phospine, such as PPh$_3$ or PBu$_3$, under an inert atmosphere and in a suitable deoxigenated solvent, such as toluene, dioxane, water, an alcohol, tetrahydrofuran or a mixture thereof, generally at temperatures ranging between 50 and 100° C.

To introduce a substituted aminocarbonyl radical (Scheme 1, reaction (l)). a reaction of an isocyanates on a compound according to Formula (IVa) may be used in the presence of an alkyl-lithium derivative, such as n-butyllithium, under an inert atmosphere and in a dry solvent, such as tetrahydrofuran, at low temperatures ranging between −78° C. and 0° C.

The substituents $R^1$ and $R^2$ may be changed or interconverted into each other by methods well known in the art, such as, for instance, reduction, substitution, acylation, a Mitsunobu reaction or reductive amination. As an example, a number of such reactions are shown in Scheme 1 below for an intermediate compound according to Formula (IVa). It is obvious that the reactions shown may also be performed on compounds according to Formula (IVb) or Formula (IVc). For ease of reading, only the phenyl part of the compound according to Formula (IVa) is shown in Scheme 1.

For instance, a reduction of an aldehyde compound (reaction (c)) may be carried out in the presence of a suitable reducing agent, for example borohydride in a suitable reaction-inert solvent, such as water, an alcohol, tetrahydrofuran or a mixture thereof, generally at room temperature.

An ether compound may be prepared (reaction (d)) by an O-alkylation reaction on the alcohol compound, using e.g. an alkyl halide The reaction may be performed in a reaction-inert solvent, such as tetrahydrofuran, in the presence of a suitable base, such as sodium hydride, optionally in the presence of potassium iodide. Convenient reaction temperatures range between 0° C. and room temperature. Alternatively, instead of alkylhalide, also alkyloxyalkylhalide or alkyloxyalkyloxyalkylhalide may be used to introduce an alkyloxyalkyl radical or an alkyloxyalkyloxyalkyl radical.

Alternatively, an alcohol compound may be reacted with an acylating agent such as an acid anhydride or an acyl halide (reaction (e)). Said reaction may be carried out in a reaction-inert solvent such as dichloromethane, chloroform or tetrahydrofuran and in the presence of a suitable base such as pyridine, triethylamine or diisopropylethyl-amine, or even without a solvent, instead using an excess of base as solvent, at temperatures ranging between 0° C. and room temperature.

Alternatively, an alcohol compound may be reacted with an aromatic or hetero-aromatic alcohol (Mitsunobu reaction, reaction (f)). This reaction may be carried out in the presence of a phosphine, such as triphenylphosphine and an azodicarboxylate derivative such as diethyl azodicarboxylate or dimethylazodicarboxylate, under an inert atmosphere and in a reaction-inert solvent such as tetrahydrofuran at temperatures ranging from room temperature to 80° C.

An aldehyde compound may also be reacted with a secondary amine using a reductive amination reaction (reaction (g)) to arrive at a secondary aminoalkyl-substituted compound. This reaction may be carried out in the presence of a suitable reducing agent, for example, sodium borohydride, sodium cyanoborohydride or sodium triacetoxyborohydride, optionally in the presence of in inorganic acid such as acetic acid or a Lewis acid, for example zinc bromide or zinc chloride, in a suitable solvent such as dichloromethane, 1,2-dichloroethane, water, an alcohol, tetrahydrofuran or a mixture thereof, and generally at room temperature.

An aldehyde compound may also be converted to an oxime-compound (reaction (h)) using art-known techniques, such as using hydroxylamines in the presence of a base such as triethylamine, $NaHCO_3$ or pyridine in a reaction inert solvent, for example ethanol or even without a solvent, using in this case excess of base as solvent, at temperatures ranging from 0° C. and room temperature.

An oxime-compound may be further converted into a nitrile (reaction (i)) in the presence of a ruthenium catalyst, such as $[RuCl_2(p\text{-cymene})]_2$ and a dehydrating agent, for example 4 Å molecular sieves, in an inert solvent, such as acetonitryle, at temperatures ranging between 50° C. and 80° C. Aminoalkyl-substituted compounds may be prepared using procedures known in the art, for instance by reduction of a nitrile compound (reaction (j)) in the presence of a suitable reducing agent, for example, lithium aluminium hydride or diisobutyl aluminium hydride, under an inert atmosphere and in a dry solvent, such as tetrahydrofuran at low temperatures ranging between −78° C. and 0° C. Further, said aminoalkyl-substituted compounds may be reacted with an acylation agent (reaction (k)), for example acyl chloride or an acid anhydride in a reaction inert solvent, such as dichloromethane, chloroform or tetrahydrofuran, in the presence of a suitable base such as pyridine, triethylamine or diisopropylethylamine, or even without a solvent, using in this case excess of base as solvent at temperatures ranging from 0° C. and room temperature.

Scheme 1

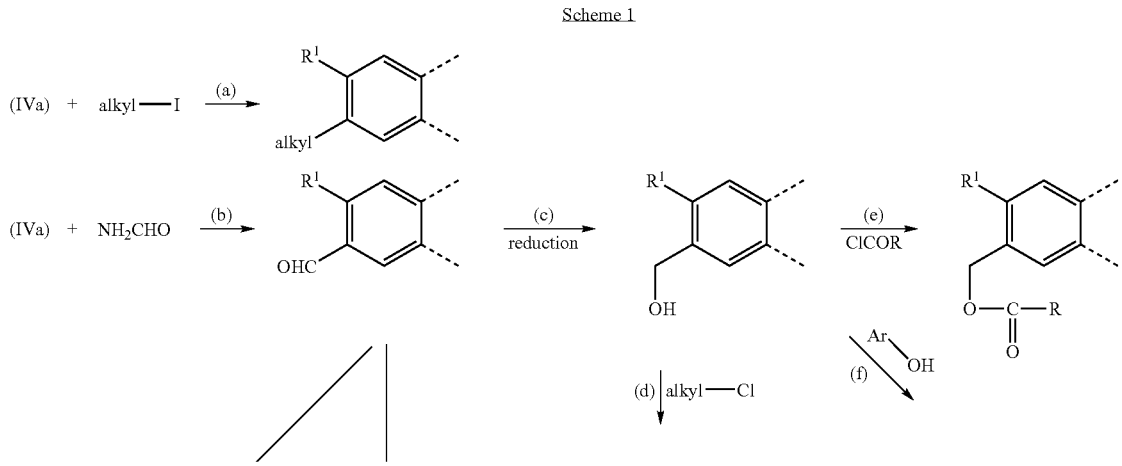

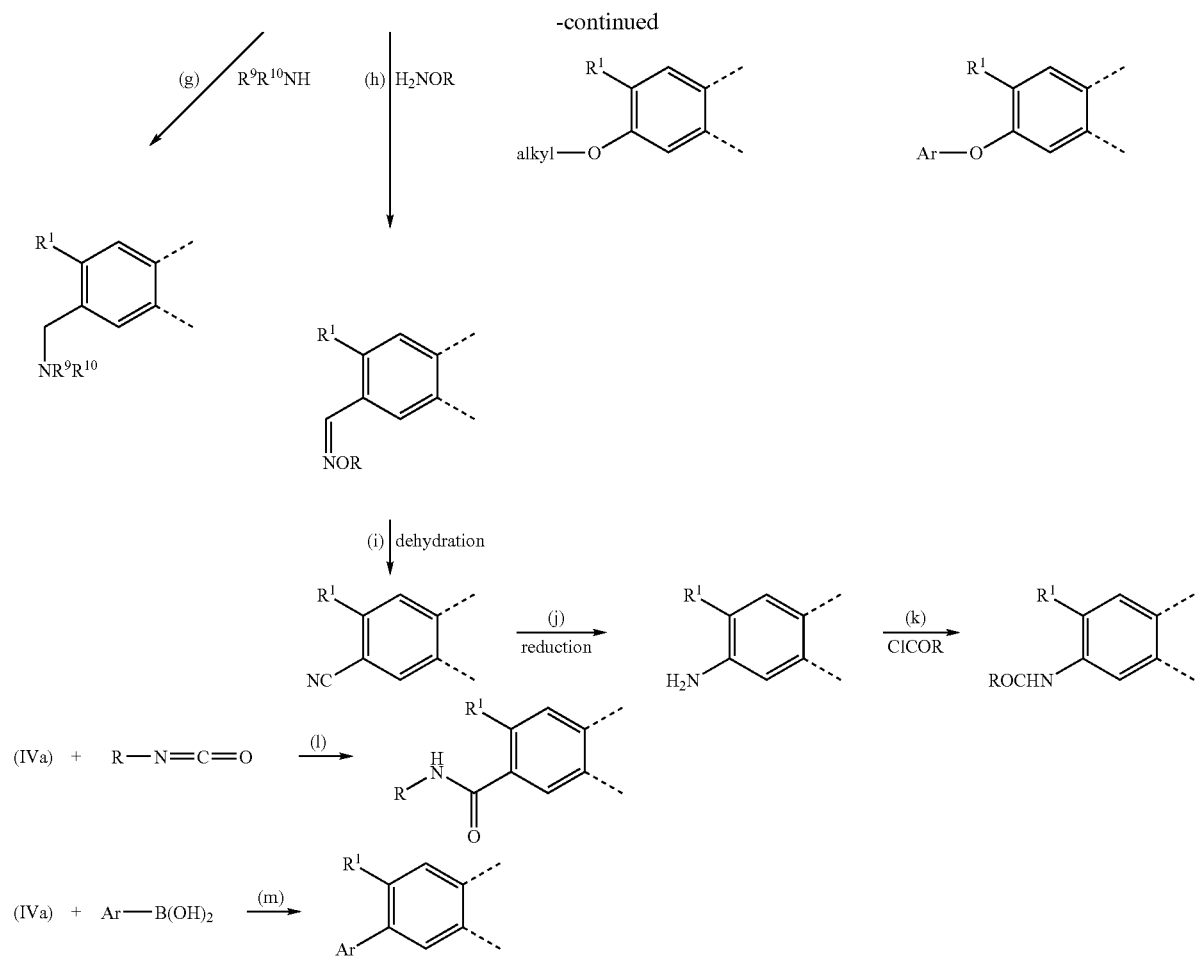

Compounds with alkyl radicals or hydrogen atoms at positions $R^1$ and/or $R^2$ can also be obtained directly with intermediate compounds that already contain said alkyl radicals or hydrogen atoms. As an example, a synthesis scheme (Scheme 2) is given for a compound according to Formula (I), with $R^1$ being a methyl and $R^2$ being a hydrogen. It is obvious that chemical equivalents may be obtained according to an equivalent synthesis pathway.

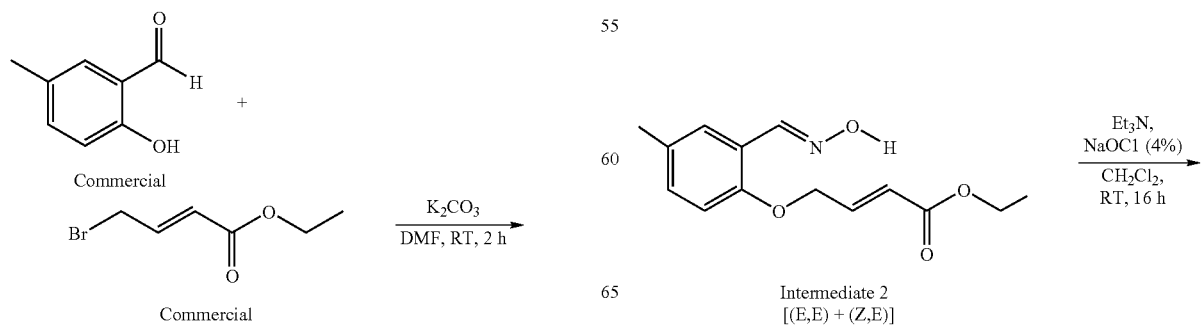

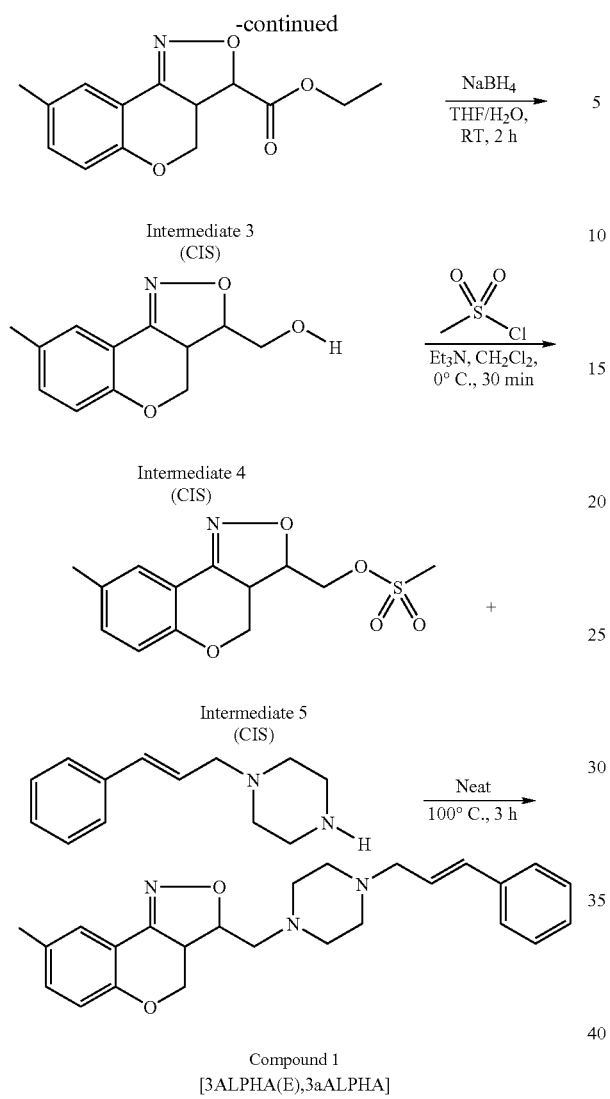

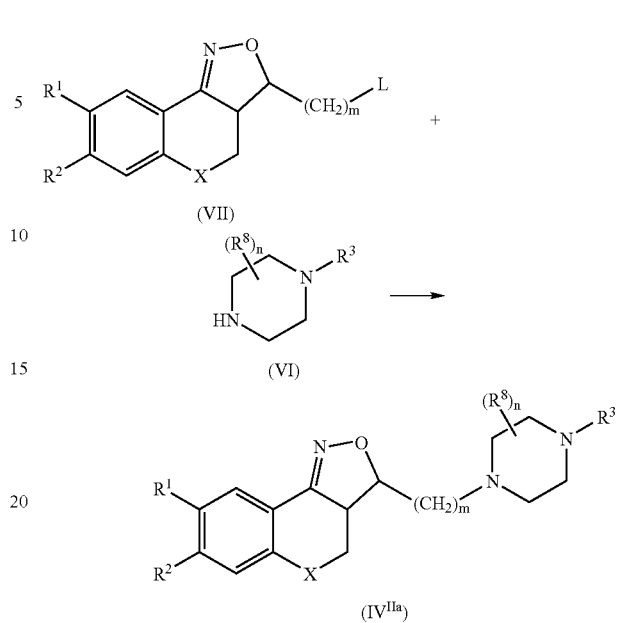

In the intermediate compound according to Formula (VII), L represents any suitable reactive leaving group, in particular halo, such as chloro, bromo or iodo or sulfonyloxy, such as methylsulphonyloxy or 4-methylbenzenesulfonyloxy.

The compounds according to Formula (IV$^{IIa}$) can also be prepared by a 2-step reaction procedure in which an intermediate compound according to Formula (VII) is first reacted (step 1) with a substituted piperazine according to Formula (VII) after which the R$^3$-radical is introduced into the resulting intermediate compound according to Formula (IX) (step 2). Reaction conditions are similar to those described above for intermediate compounds according to Formula (IV$^{IIa}$).

The starting materials and some of the intermediate compounds are compounds that are either commercially available or may be prepared according to conventional reaction procedures generally known in the art.

The intermediate compounds, in particular the intermediate compounds according to Formula (IV), more in particular according to Formula (IVa), (IVb) and (IVc) can be prepared according to various ways.

In particular, the intermediate compounds according to Formula (IV$^{IIa}$), i.e. intermediate compounds according to Formula (IV) with a Pir-radical according to Formula (IIa) can be prepared by a nucleophilic substitution reaction with a substituted piperazine according to Formula (VI) on an intermediate compound according to Formula (VII). These reactions may be carried out in a reaction inert solvent such as dioxane, methylisobutylketone or N,N'-dimethylformamide, in the presence of a suitable base such as potassium carbonate, sodium carbonate or triethylamine, or even without a base, using in this latter case excess of reagent of Formula (VI). Convenient reaction temperatures range between 100° C. and 150° C.

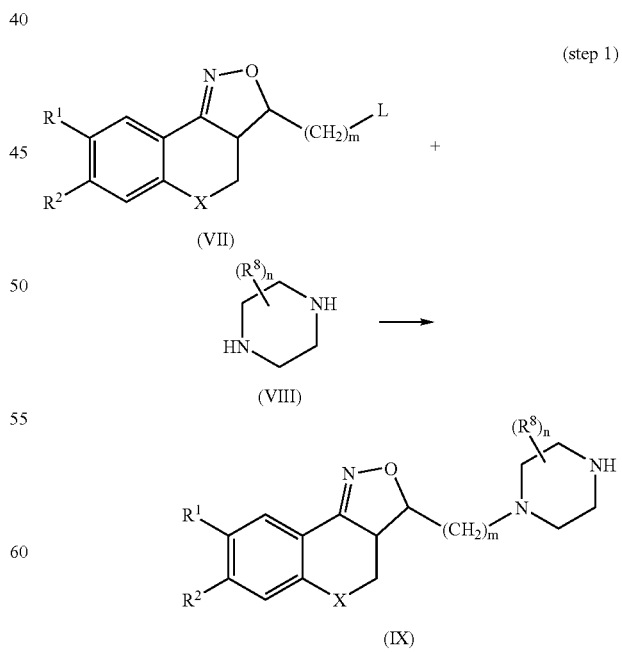

In intermediate compound according to Formula (VII), L represents any suitable reactive leaving group, in particular halo, such as chloro, bromo or iodo or sulfonyloxy, such as methylsulphonyloxy or 4-methylbenzenesulfonyloxy.

One of the nitrogen functions of the substituted piperazine of Formula (VIII) may also be protected, e.g. by a tert-butyloxycarbonyl-group.

(step 2)

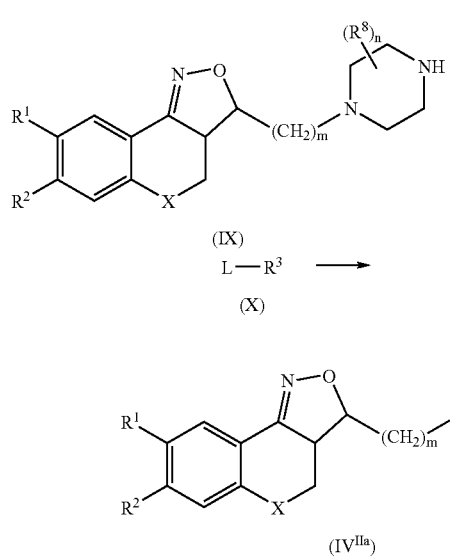

In the compound according to Formula (X), L represents any suitable reactive leaving group, in particular halo, such as chloro, bromo or iodo or sulfonyloxy, such as methylsulphonyloxy or 4-methylbenzenesulfonyloxy. Also, $R^3$—CHO may be used instead of a compound according to Formula (X) wherin $R^3$ has the same meaning as in Formula (I).

The compounds according to Formula (IV$^{IIa}$) can also be prepared by a 2-step reaction procedure in which an intermediate compound according to Formula (IX) is reacted with an acid according to Formula (XI) (step 1), followed by a subsequent reduction of the carbonyl-function of the intermediate compound according to Formula (XII) (step 2). Reactions of step 1 may be carried out in a reaction inert solvent, such as chloroform, dichloromethane, tetrahydrofuran, dimethylformamide or a mixture thereof, using any of methods known to a person skilled in the art using condensation reagents such as 1,1'-carbonyldiimidazole, N,N'-dicyclohexylcarbodiimide or by previous transformation of carboxylic acid of Formula (XI) into its corresponding acid chloride. Reactions shown in step 2 can be performed using a suitable reducing agent, such as lithium-aluminum hydride or aluminum hydride, in a suitable solvent, for example tetrahydrofuran. Generally, these reactions are run at a temperature ranging between $-20°$ C. and room temperature.

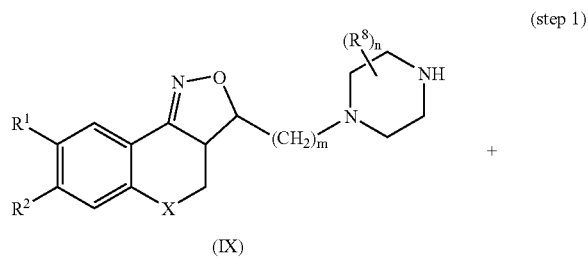

-continued

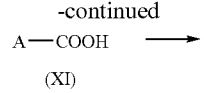

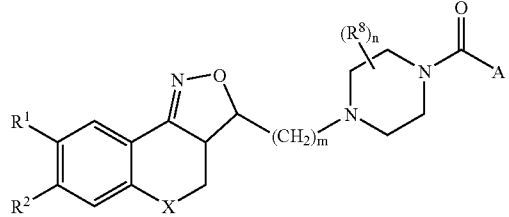

(step 2)

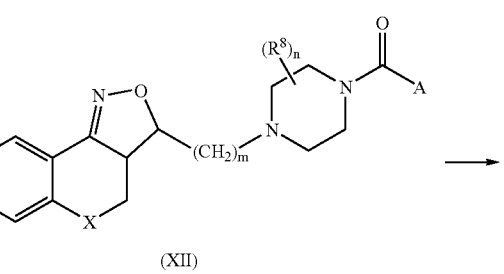

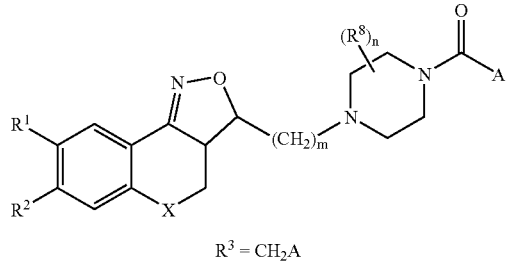

In the intermediate compounds according to Formula (XI), (XII) and (XIII), the A-group represents an optionally substituted aromatic homocyclic or heterocyclic ring system including a partially or completely hydrogenated hydrocarbon chain of maximum 5 atoms long of which one or more carbon atoms may be replaced by one or more atoms selected from the group of oxygen, nitrogen and sulphur, with which the ring system is attached to the Pir radical that has been defined above.

Intermediate compounds according to Formula (VII) in which X=O may be prepared according to the following reaction:

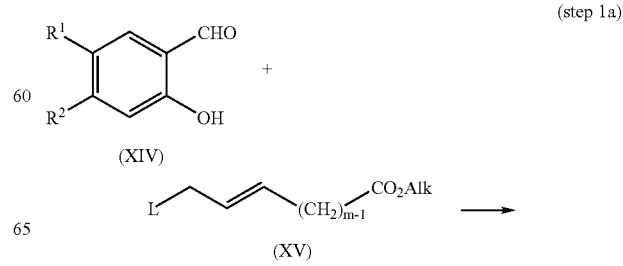

-continued

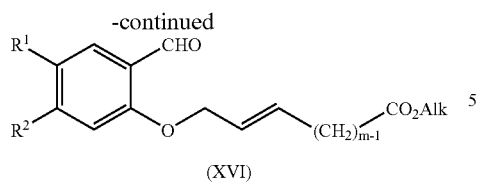

(XVI)

In intermediate compound according to Formula (XV), L represents any suitable reactive leaving group, in particular halo, such as chloro, bromo or iodo or sulfonyloxy, such as methylsulphonyloxy or 4-methylbenzeiesulfonyloxy. Furthermore, Alk in intermediate compound according to Formula (XV) represents any $C_{1-6}$ alkyl-group, in particular an ethyl-group and m is defined as in Formula (I).

Intermediate compounds according to Formula (VII) in which X=NH may also be prepared in an equivalent manner according to above step 1a, provided that the intermediate compound according to Formula (XIV) is replaced by its amine-analog of Formula (XVII), preferably with the amine group protected with e.g. a $COCF_3$— group. The alkylation step may be carried out in a reaction inert solvent, for example, tetrahydrofuran or dimethylformamide, in the presence of a strong base, such as sodium or potassium hydride, and the addition of a crown-ether, such as 18-crown-6 or 15-crown-5. Convenient reaction temperatures range between room temperature and 60° C.

(step 1b)

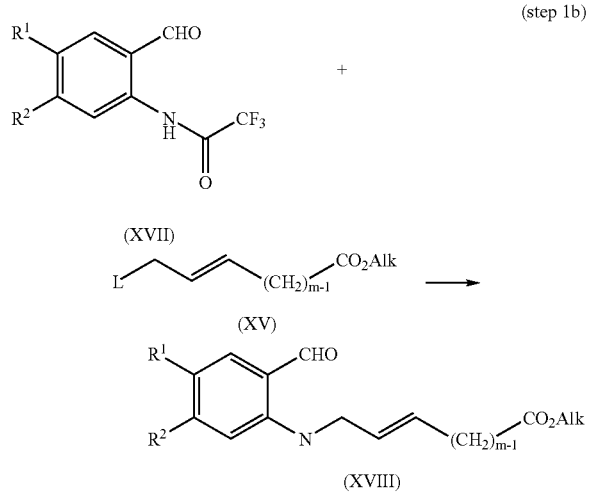

Intermediate compounds according to Formula (XVIII) are converted to oximes of Formula (XIX) using art-known techniques, such as using hydroxylamine hydrochloride in the presence of $NaHCO_3$ or pyridine in a reaction inert solvent, for example ethanol (step 2).

(step 2)

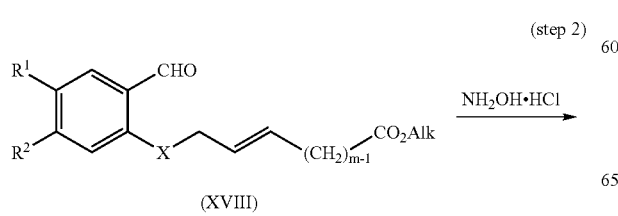

(XVIII)

-continued

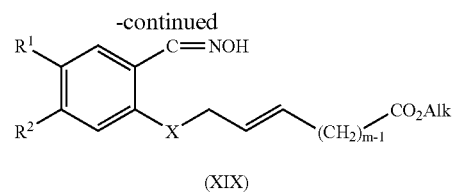

(XIX)

Intermediate compounds according to Formula (XIX) are oxidized to their nitril oxides and undergoes in situ an intramolecular cycloaddition, yielding intermediate compounds according to Formula (XX). This oxidation can be carried out using a sodium hypochlorite solution in the presence of triethylamine in an inert solvent such as dichloromethane at room temperature. Oxidation can also be performed using Chloramine-T (N-chloro-4-methylbenzenesulfonamide, sodium salt), stirring and heating in a solvent such as refluxing ethanol. At this stage the two stereocenters a and b of Formula (IV) are formed.

(step 3)

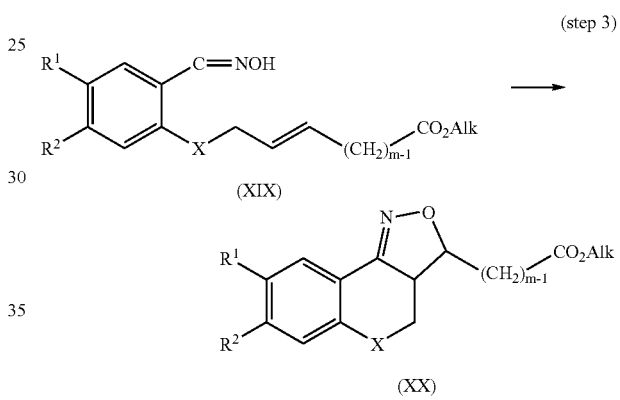

Preparation of an intermediate compound according to Formula (XXI) can be achieved using procedures known in the art, for instance by reduction of the carbonyl compound according to Formula (XX) in the presence of a suitable reducing agent, for example, sodiumborohydride in a suitable solvent, such as water, an alcohol, tetrahydrofuran or a mixture thereof, generally at room temperature.

(step 4)

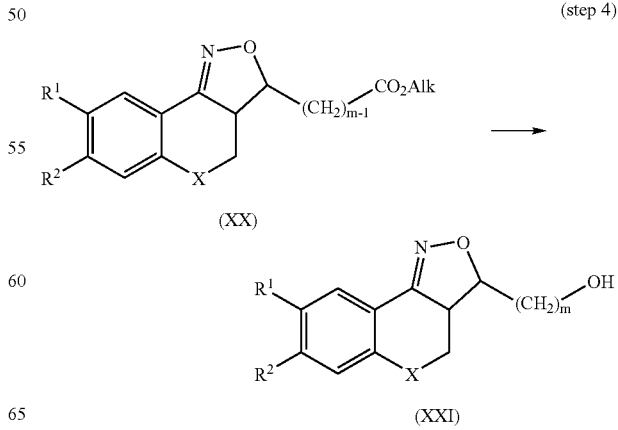

The intermediate compound according to Formula (VII) can be prepared from intermediate compound according to Formula (XXI) using standard techniques. Thus, reaction with methanesulfonyl chloride or 4-methylbenzenesulfonyl chloride in the presence of a base, such as triethylamine, in a reaction inert solvent, for example dichloromethane, at reaction temperatures ranging between 0° C. and room temperature, yields the corresponding sulfonyloxy derivative intermediate compound according to Formula (VII). The corresponding halo-derivative can also be prepared, e.g. treating intermediate compound according to Formula (XXI) with triphenylphosphine, in the presence of tetrachloromethane, in a reaction inert solvent, such as tetrahydrofuran, stirring and refluxing the mixture.

ran, at low temperatures ranging between −78° C. and 0° C., yielding an intermediate compound according to Formula (XXVII). The intermediate compound according to Formula (XXVIII) may be prepared by reaction of intermediate compound according to Formula (XXVII) with hydroxylamine, in the presence of a base such as sodium bicarbonate, in a solvent such as a lower alkyl-alcohol like ethanol, generally at room temperature. Finally, the oxidation of the oxime derivative of Formula (XXVIII) to its nitril oxide and subsequent in situ cycloaddition to give an intermediate compound according to Formula (XXIX), may be achieved by similar standard techniques such as those described above for intermediate compound according to Formula (XIX) to give intermediate compounds according to Formula (XX).

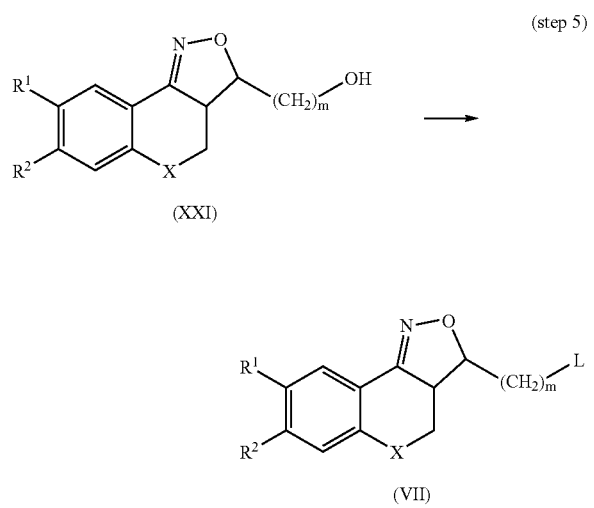

It is evident that in the foregoing and in the following reactions, the reaction products may be isolated from the reaction medium and, if necessary, further purified according to methodologies generally known in the art such as extraction, crystallization and chromatography. It is further evident that reaction products that exist in more than one enantiomeric form, may be isolated from their mixture by known techniques, in particular preparative chromatography, such as preparative HPLC. Typically, intermediate compounds (VII) and (IV) and final compounds according to Formula (I) may be separated into their enantiomeric forms.

Compounds according to the invention in which $X=CH_2$ may be prepared according to the following reaction scheme (Scheme 3) in which an intermediate compound according to Formula (VI) is first N-alkylated with a dihaloderivative of Formula (XXII) using standard techniques, in the presence or absence of a base and in an inert reaction solvent, such as chloroform, dichloromethane or 1,2-dichloroethane, and at reaction temperatures ranging between room temperature and 80° C., yielding an intermediate compound according to Formula (XXIII). An aldehyde of Formula (XXIV) is reacted with tert-butylamine (XXV) in an aprotic solvent such as toluene, stirring and heating at reflux temperature with removal of water using a standard device, such as a Dean-Stark water separator, yielding an imine of Formula (XXVI). C-alkylation of intermediate compound according to Formula (XXVI) with intermediate compound according to Formula (XXIII) can be achieved in the presence of an alkyl-lithium derivative, such as n-butyllithium, under an inert atmosphere and in a dry inert solvent, such as tetrahydrofu-

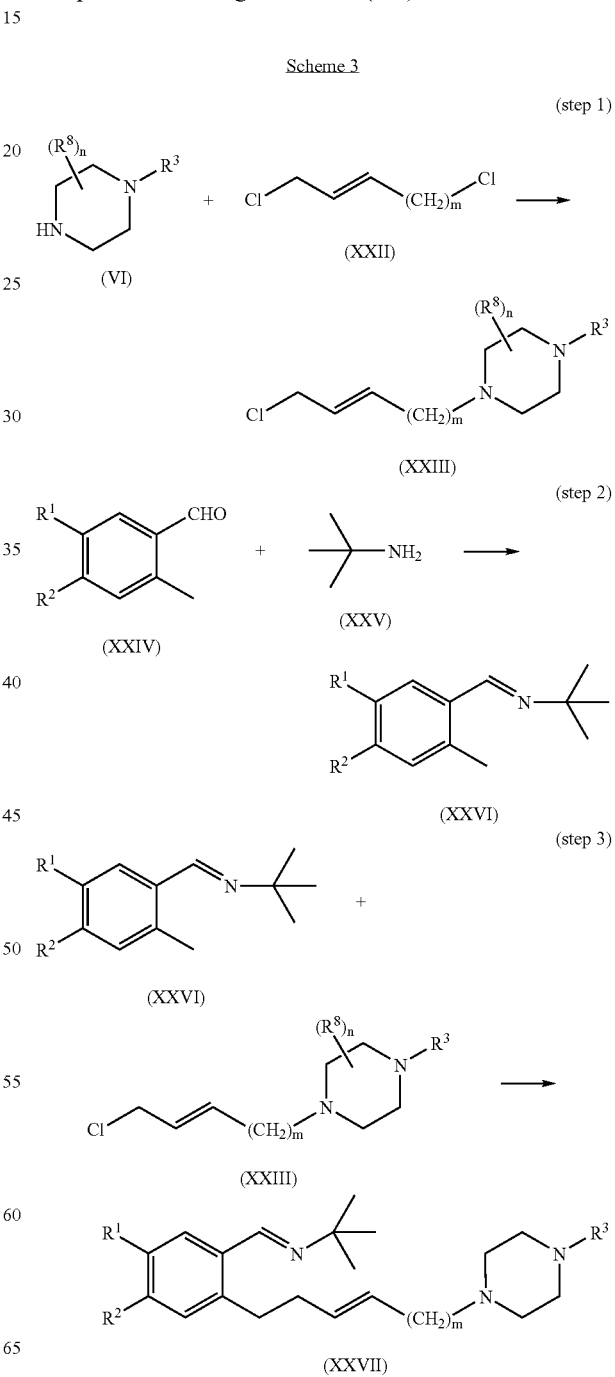

-continued

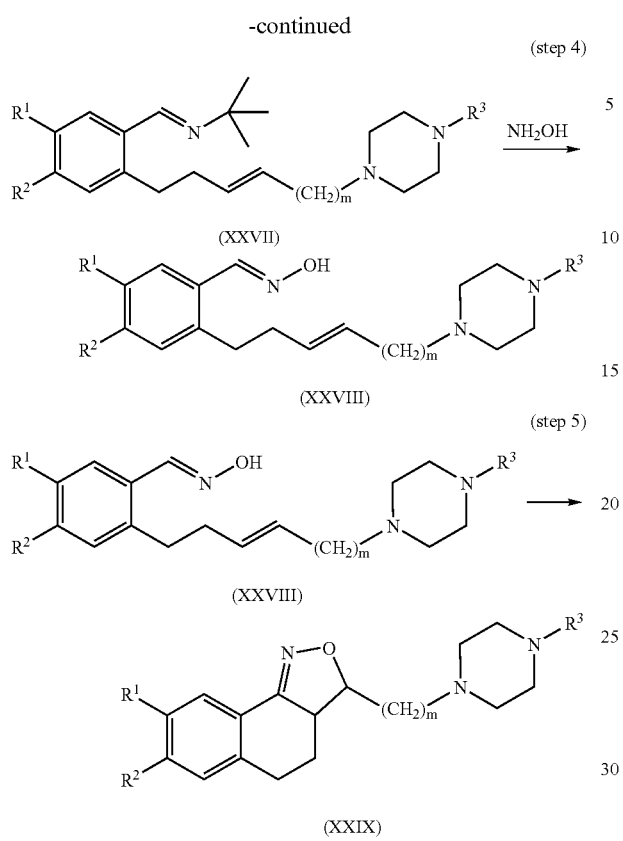

It is evident that the reaction steps disclosed above may be adapted to the specific reaction products. The reaction steps disclosed may be performed in any way known to the skilled person, including in solution or as solid phase reactions, the latter during which the reaction products are bound to a resin material and are—in a final cleavage step—released from the resin material. Examples of such embodiments and adaptations have been disclosed by way of the Examples further in this application.

The following examples illustrate the present invention without being limited thereto.

EXPERIMENTAL PART

The carbon ring numbering system for the compounds according to Formula (I) used in this application is as follows:

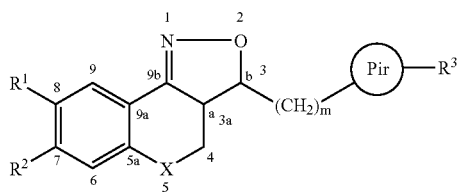

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction. The stereogenic centers a and b in compounds according to Formula (I) have respectively the ring numbers 3a and 3.

Hereinafter, "DMF" is defined as N,N-dimethylformamide, "DIPE" is defined as diisopropyl ether, and "THF" is defined as tetrahydrofurane.

A. Preparation of the Intermediate Compounds

EXAMPLE A.1

Preparation of Intermediate Compound 1

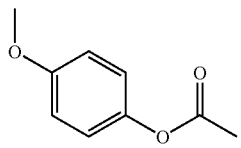

To a solution of

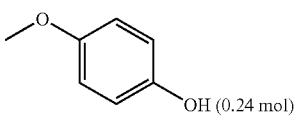

(0.24 mol) and $Et_3N$ in $CHCl_3$ (1000 ml) acetyl chloride (0.29 mol) was dropwise added. The mixture was stirred at room temperature for 24 hours and then a saturated aqueous solution of $NaHCO_3$ was added. The organic layer was separated, dried ($Na_2SO_4$), filtered and the solvent evaporated. Yield 49.6 g of intermediate compound 1 used in next step without further purification (quantitative).

Preparation of Intermediate Compound 2

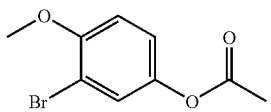

N-Bromosuccinimide (0.24 mol) was added to a solution of intermediate compound 1 (0.24 mol) in $CH_3CN$ (1000 ml). The mixture was stirred at room temperature for 24 hours and then more N-bromosuccinimide (0.24 mol) was added. After 24 hours of stirring the solvent was evaporated and the residue partitioned between $H_2O$ and diethyl ether. The organic layer was separated, dried ($Na_2SO_4$), filtered and the solvent evaporated. Yield 72 g of intermediate compound 2 used in next step without further purification (quantitative).

Preparation of Intermediate Compound 3

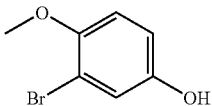

A solution of KOH (0.26 mol) in H$_2$O (130 ml) was added to a solution of intermediate compound 2 (0.24 mol) in MeOH (920 ml). The mixture was stirred at room temperature for 45 minutes and then more H$_2$O was added (250 ml). The mixture was acidified by 2M aqueous solution of HCl addition and extracted with CH$_2$Cl$_2$. The organic layer was separated, dried (Na$_2$SO$_4$), filtered and the solvent evaporated. Yield 44 g of intermediate compound 3 used in next step without further purification (90%).

Preparation of Intermediate Compound 4

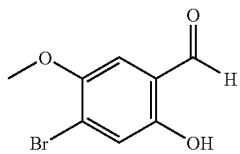

A mixture in MeOH (88 ml) of magnesium (0.13 mol) and 8% solution of Mg(OMe)$_2$ in MeOH (2.64 ml) was heated under reflux until complete magnesitun dissolution and hydrogen evolution was ceased. Then intermediate compound 3 (0.22 mol) and toluene (400 ml) were added and the azeotropic mixture of MeOH and toluene was evaporated at 507 mbar of pressure until the temperature of the reaction mixture rose to 75° C. At this moment paraformaldehyde (0.65 nmol) was added to the mixture over 1 hour at 75° C., with concurrent removal of volatile materials by evaporation at 507 mbar of pressure, additional toluene (100 ml) was added to maintain fluidity of the resulting slurry. Stirring was continued at 75° C. and 374 mbar of pressure for 3 hours after which 10% sulphuric acid was added to the mixture. The mixture was stirred for 30 minutes and then the organic layer was separated and evaporated. The residue was purified by short open column chromatography over silica gel (eluent CH$_2$Cl$_2$). Yield 20.86 g (42%).

Preparation of Intermediate Compound 5

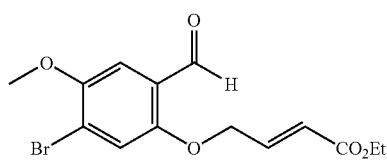

To a solution of intermediate compound 4 (0.09 mol) in DMF (110 ml), at 0° C., K$_2$CO$_3$ (0.18 mol) and ethyl 4-bromocrotonate (0.14 mol) were added. The mixture was stirred at room temperature for 4 hours and then partitioned between H$_2$O and CH$_2$Cl$_2$. The organic layer was separated, dried (Na$_2$SO$_4$), filtered and the solvent evaporated. The residue was purified by short open column chromatography over silica gel (eluerit heptane/AcOEt 80/20). Yield 9.30 g (30%).

Preparation of Intermediate Compound 6

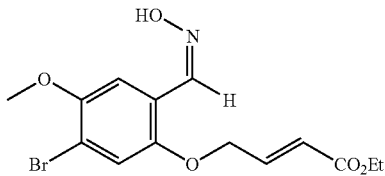

To a mixture of intermediate compound 5 (0.032 mol) and AcONa (0.048 mol) in EtOH (100 ml), at 0° C., hydroxylamine hydrochloride (0.039 mol) was added. The mixture was stirred at 0° C. for 3 hours and then was partitioned between H$_2$O and CH$_2$Cl$_2$. The organic layer was separated, dried (Na$_2$SO$_4$), filtered and the solvent evaporated. Yield 11.3 g of intermediate compound 6 used in next step without further purification (98%).

Preparation of Intermediate Compound 7

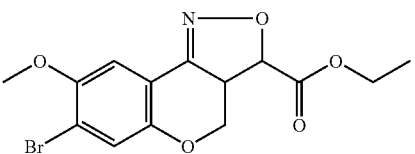

A 4% aqueous solution of NaClO (88 ml) was dropwise added, at 0° C., to a solution of intermediate compound 6 (0.026 mol) in CH$_2$Cl$_2$ (250 ml). The mixture was stirred at room temperature for 2 hours and then, after cooling to 0° C., Et$_3$N (0.039 mol) was dropwise added. The resulting mixture was stirred at room temperature for 24 additional hours and then the organic layer was separated, dried (Na$_2$SO$_4$) filtered and evaporated. The residue was purified by short open column chromatography over silica gel (eluent heptane/AcOEt 80/20, 70/30 and 60/40). Yield 8.43 g (91%).

Preparation of Intermediate Compound 8

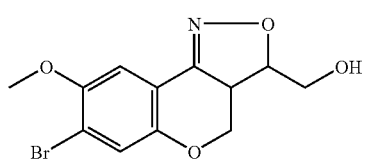

NaBH$_4$ (0.059 mol) was portionwise added to a solution of intermediate compound 7 (0.024 mol) in a mixture of TIE (180 ml) and H$_2$O (18 ml), previously cooled at 0° C. The mixture was stirred at room temperature for 24 hours and then a 10% aqueous solution of NH$_4$Cl was added. The resulting mixture was extracted with CH$_2$Cl$_2$ and the organic layer was separated, dried (Na$_2$SO$_4$) filtered and the solvent evaporated. Yield 7.85 g of intermediate compound 8 used in next step without further purification (quantitative).

Preparation of Intermediate Compound 9

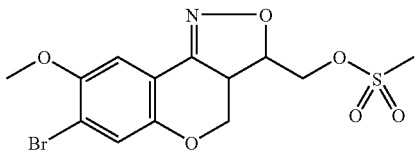

To a solution of intermediate compound 8 (0.024 mol) and Et₃N (0.036 mol) in CH₂Cl₂ (105 ml), at 0° C., mesyl chloride (0.026 mol) was added. The mixture was stirred at 0° C. for 2 hours and then a saturated aqueous solution of NaHCO₃ was added. The organic layer was separated, dried (Na₂SO₄) filtered and the solvent evaporated. Yield 9.6 g of intermediate compound 9 used in next step without further purification (quantitative).

Preparation of Intermediate Compound 10

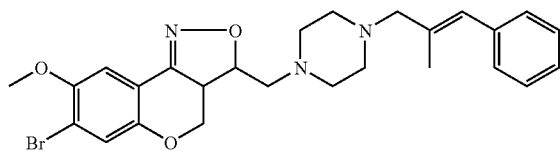

A mixture of intermediate compound 9 (0.0076 mol),

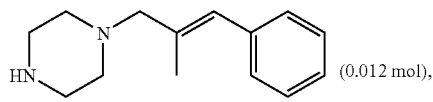 (0.012 mol),

KI (0.0076 mol) and K₂CO₃ (0.0076 mol) in methyl isobuthyl ketone (35 ml) was stirred and refluxed for 24 hours. Then the mixture was partitioned between H₂O and CH₂Cl₂ and the organic layer was separated, dried (Na₂SO₄) filtered and the solvent evaporated. The residue was purified by short open column chromatography over silica gel (eluent CH₂Cl₂/(CH₃OH/NH₃) 99/1). Desired fractions were collected and evaporated and the residue precipitated from DIPE. Yield 2.2 g (56%).

EXAMPLE A.2

Preparation of Intermediate Compound 11

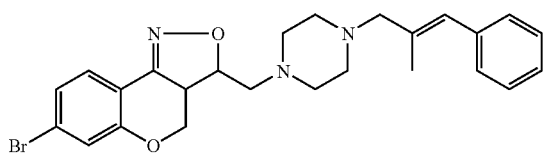

Intermediate compound 11 was prepared in a way equivalent to intermediate compound 10 (according to A.1.).

B. Preparation of the Final Compounds

EXAMPLE B.1

Preparation of Final Compound 2

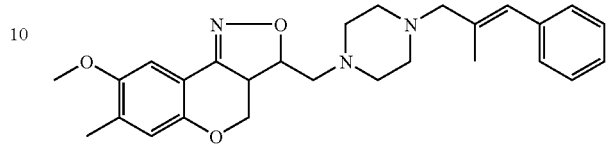

To a solution of intermediate compound 10 (0.00039 mol) in THF (5 ml), at −78° C. under N₂, a solution 2.5 M of n-butyllithium in hexanes (0.00043 mol) was dropwise added. The mixture was stirred at −78° C. for 1 hour and then methyliodide (0.0019 mol) was added. The resulting mixture was stirred at −78° C. for 1 additional hour and then a 5% aqueous solution of HCl was added. The organic layer was separated and the aqueous layer was extracted with CH₂Cl₂. The combined organic extracts were dried (Na₂SO₄) filtered and the solvent evaporated. The residue was purified by short open column over silica gel (eluent CH₂Cl₂/MeOH 98/2). The product containing fractions were collected and evaporated and the residue purified again by reverse phase HPLC (eluent CH₃CN/0.05% aqueous solution of AcONH₄ 75/25). Desired fractions were collected, the CH₃CN evaporated and the resulting aqueous suspension extracted with AcOEt. The organic layer was separated, dried (Na₂SO₄), filtered and the solvent evaporated. Yield: 0.047 g of compound 2 (27%).

EXAMPLE B.2

Preparation of Final Compound 3

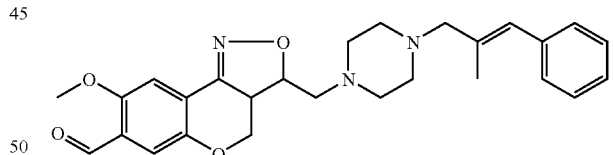

To a solution of intermediate compound 10 (0.00039 mol) in THF (5 ml), at −78° C. under N₂, a solution 2.5 M of n-butyllithium in hexane (0.00043 mol) was dropwise added. The mixture was stirred at −78° C. for 15 minutes and then anhydrous DMF (0.0078 mol) was added. The resulting mixture was stirred at −78° C. for 45 additional minutes and then a 10% aqueous HCl solution was added. The organic layer was separated and the aqueous layer was extracted with CH₂Cl₂. The combined organic extracts were dried (Na₂SO₄) filtered and the solvent evaporated. The residue was used in next step without further purification. Yield: 0.0172 g of compound 3 (95%).

Preparation of Final Compound 19

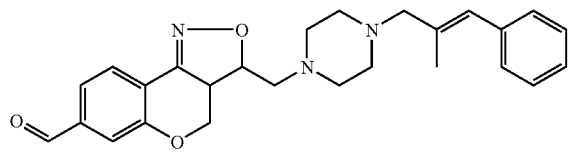

Compound 19 was prepared in the same way as compound 3, starting from intermediate compound 11.

Preparation of Final compound 4

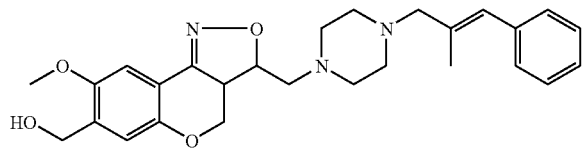

NaBH$_4$ (0.00053 mol) was added portionwise to a solution of final compound 3 (0.00021 mol) in THF (10 ml) and H$_2$O (1 ml), at 0° C. The mixture was stirred at room temperature for 1.5 hours and then a 10% aqueous NH$_4$Cl solution was added. The resulting mixture was extracted with CH$_2$Cl$_2$ and the organic layer was dried (Na$_2$SO$_4$) filtered and evaporated. The residue was purified by Sep-Pak Silica Cartridge chromatography (eluent CH$_2$Cl$_2$/CH$_3$OH 99/1 and 98/2). The product fractions were collected and the solvent evaporated. The residue was converted in its hydrochloric acid salt in IPA. The salt was filtered, triturated from DIPE, then dried. Yield: 0.031 g.

Preparation of Final Compound 6

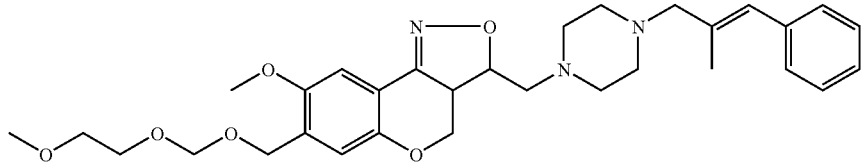

A solution of final compound 4 (0.00026 mol) in THF (5 ml) was dropwise added to a suspension of NaH (0.00052 mol) in THF (10 ml) cooled to 0° C. The resulting mixture was stirred at 0° C. for 20 minutes and then IK (0.00040 mol) and 2-methoxyethoxymethyl chloride (0.00040 mol) were added. The mixture was stirred at room temperature overnight and then a 10% aqueous NH$_4$Cl solution was added and this mixture was extracted with CH$_2$Cl$_2$. The separated organic layer was dried (Na$_2$SO$_4$) filtered and evaporated. The residue was purified by short open column chromatography over silica gel (eluent CH$_2$Cl$_2$/(CH$_3$OH/NH$_3$) 99/1). Desired fractions were collected and the solvent evaporated. The residue was converted in its ethano dioic acid salt in EtOH. The salt was filtered, triturated from DIPE, then dried. Yield: 0.033 g (19%).

EXAMPLE B.3

Preparation of Final Compound 7

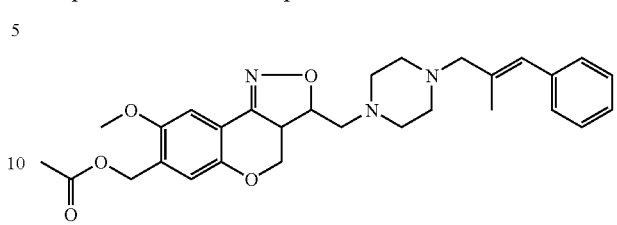

A mixture of final compound 4 (0.00025 mol), acetic anhydride (7 ml) and pyridine (5 ml) was stirred overnight, at room temperature. The volatiles were evaporated under reduced pressure and the residue was purified by Sep-Pak Silica Cartridge chromatography (eluent CH$_2$Cl$_2$/(CH$_3$OH/NH$_3$) 99/1). Desired fractions were collected and the solvent evaporated. The residue was converted in its ethano dioic acid salt in EtOH. The salt was filtered, triturated from DIPE, then dried. Yield: 0.054 g (24%).

EXAMPLE B.4

Preparation of Final Compound 8

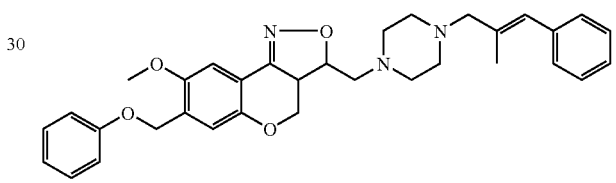

To a mixture of final compound 4 (0.00036 mol) and phenol (0.00040 mol) in THF (5 ml), in a sealed tube at room temperature under N$_2$, were added triphenylphosphine polymer supported (0.00072 mol) and diethyl azodicarboxylate (0.00045 mol). The resulting mixture was stirred at 50° C. overnight and then the mixture was filtered through a celite pad. The filtrate was extracted with H$_2$O and the organic layer was separated, dried (Na$_2$SO$_4$) filtered and the solvent evaporated. The residue was purified by Sep-Pak Silica Cartridge chromatography (eluent CH$_2$Cl$_2$/(CH$_3$OH/NH$_3$) 99/1). Desired fractions were collected and the solvent evaporated. Yield: 0.041 g (33%).

EXAMPLE B.5

Preparation of Final Compound 10

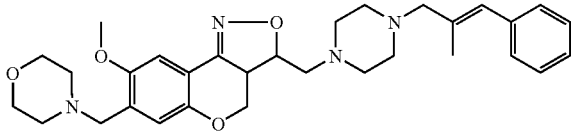

Sodium triacetoxyborohydride (0.00058 mol) was portionwise added to a mixture of final compound 3 (0.00039 mol) and morpholine (0.00043 mol) in 1,2-dichloroethane (5 ml) at −10° C. The reaction mixture was allowed to warm to room temperature and then it was stirred overnight. Then a 10% aqueous NH$_4$Cl solution was added and the mixture was stirred for 30 minutes. The organic layer was separated and the aqueous layer extracted with CH$_2$Cl$_2$. The combined organic extracts were dried (Na$_2$SO$_4$) filtered and evaporated. The residue was purified by Sep-Pak cartridge chromatography over silica gel (eluent CH$_2$Cl$_2$/(CH$_3$OH/NH$_3$) 98/2). Fractions containing product were collected and the solvent evaporated. Yield: 0.074 g (19%).

EXAMPLE B.6

Preparation of final Compound 11

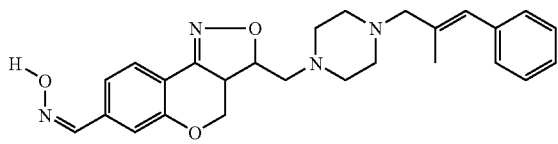

Hydroxylamine hydrochloride was added to a solution of final compound 19 (0.00042 mol) in pyridine (5 ml) at room temperature. The reaction mixture was stirred overnight and then it was partitioned between H$_2$O and CH$_2$Cl$_2$. The organic layer was separated, extracted with brine, dried (Na$_2$SO$_4$), filtered and concentrated until dryness. The residue was crystallized from CH$_3$CN. Yield: 0.099 g (53%).

EXAMPLE B.7

Preparation of Final Compound 13

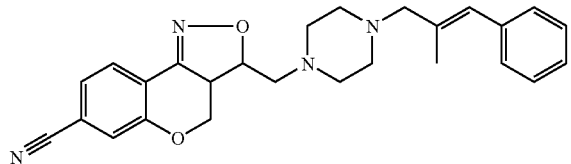

To a solution of final compound 11 (0.00061 mol) and [RuCl$_2$(p-cymene)]$_2$ in CH$_3$CN (5 ml), at room temperature, was added 4 Å molecular sieves. The mixture was stirred at reflux for 15 minutes and then filtered trough a celite pad. The filtrate was concentrated until dryness and the residue triturated from CH$_3$CN and the solid filtered and dried. Yield: 0.259 g (99%).

Preparation of Final Compound 14

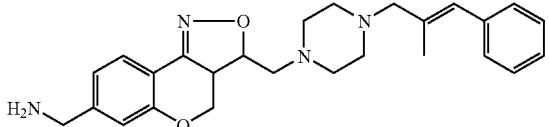

A solution 1M of LiAlH$_4$ in THF (0.00043 mol) was dropwise added to a solution of final compound 13 (0.00029 mol) in anhydrous THF (5 ml) at −20° C., under N$_2$. The mixture was stirred at 0° C. for 2 hours and then a 10% aqueous NH$_4$Cl solution was added and the resulting mixture was extracted with CH$_2$Cl$_2$. The separated organic layer was dried (Na$_2$SO$_4$), filtered and evaporated. The residue was purified by Sep-Pak Silica Cartridge chromatography (eluent CH$_2$Cl$_2$/CH$_3$OH 98/2 and 95/5). The product fractions were collected and the solvent evaporated. Yield: 0.025 g (20%).

Preparation of Final Compound 15

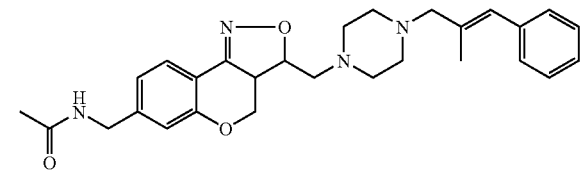

Acetic anhydride (2 ml) was added to a solution of final compound 14 (0.00053 mol) in pyridine (1 ml). The reaction mixture was stirred at room temperature for 4 hours and then volatiles were evaporated until dryness. The crude was purified by Sep-Pak Silica Cartridge chromatography (eluent CH$_2$Cl$_2$/(CH$_3$OH/NH$_3$) 99/1). Desired fractions were collected and the solvent evaporated. The residue was converted in its ethano dioic acid salt in EtOH. The salt was filtered, triturated from DIPE, then dried. Yield: 0.014 g (48%).

EXAMPLE B.8

Preparation of Final Compound 16

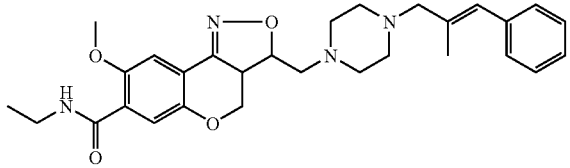

To a solution of intermediate compound 10 (0.00029 mol) in 5 ml of THF, at −78° C. under N$_2$, a solution 2.5 M of n-butyllithium in hexanes (0.00032 mol) was dropwise added. The mixture was stirred at −78° C. for 1 hour and then ethyl isocyante (0.0012 mol) was added. The resulting mixture was allowed to warm to 0° C. and then it was stirred for 2 hours. Then a 10% aqueous solution of HCl was added. The organic layer was separated and the aqueous layer was extracted with CH$_2$Cl$_2$. The combined organic extracts were dried (Na$_2$SO$_4$) filtered and the solvent evaporated. The residue was purified by Sep-Pak Silica Cartridge chromatography (eluent CH$_2$Cl$_2$/(MeOH/NH$_3$) 99/1, 98/2 and 97/3). Desired fractions were collected and evaporated The residue was precipitated from CH$_3$CN/DIPE and then filtered and dried. Yield: 0.015 g (10%).

EXAMPLE B.9

Preparation of Final Compound 17

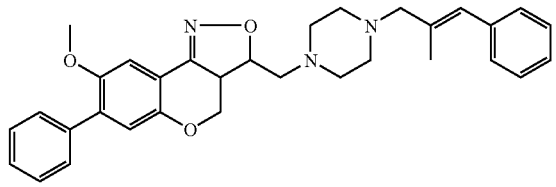

A mixture of intermediate compound 10 (0.00029 mol), phenyl boronic acid (0.00032 mol) and PPh$_3$ (cat) in a mixture of toluene (5 ml), EtOH (1 ml) and 1 M aqueous solution of Na$_2$CO$_3$ (1 ml) was stirred at reflux under N$_2$ for 16 hours. Then the organic layer was separated and the aqueous layer extracted with AcOEt. The combined organic extracts were dried (Na$_2$SO$_4$) filtered and the solvent evaporated. The residue was purified by Sep-Pak Silica Cartridge chromatography (eluent CH$_2$Cl$_2$/MeOH 99/1 and 98/2). Desired fractions were collected and evaporated and the residue crystallized from CH$_3$CN/DIPE, filtered and dried. Yield: 0.048 g (32%).

TABLE 1

| Co. no. | Exp. no. | —R$^1$ | ---R$^2$ | ---R$^4$ | --R$^6$ | Phys. data |
|---|---|---|---|---|---|---|
| 1 | Scheme 1 | —CH$_3$ | —H | —H | —H | [3α(E),3aα] m.p. 123.3 |
| 2 | B1 | —OCH$_3$ | —CH$_3$ | —CH$_3$ | —H | [3a(E),3aα] |
| 23 | B5 | —OCH$_3$ | cyclopropyl-CH$_2$– | —CH$_3$ | —F | [3a(E),3aα] |
| 4 | B2 | —OCH$_3$ | —CH$_2$OH | —CH$_3$ | —H | [3a(E),3aα] HCl(1:2) |
| 5 | B2 | —H | —CH$_2$OCH$_3$ | —CH$_3$ | —H | [3α(E),3aα] HCl(1:2) |
| 6 | B2 | —OCH$_3$ | —CH$_2$OCH$_2$CH$_2$OCH$_3$ | —CH$_3$ | —H | [3a(E),3aα] C$_2$H$_2$O$_4$(1:1) |
| 7 | B3 | —OCH$_3$ | —CH$_2$OC(O)CH$_3$ | —CH$_3$ | —H | [3a(E),3aα] |
| 8 | B4 | —OCH$_3$ | —CH$_2$OPh | —CH$_3$ | —H | [3a(E),3aα] C$_2$H$_2$O$_4$(1:1) |
| 14 | B7 | —H | —CH$_2$—NH$_2$ | —CH$_3$ | —H | [3a(E),3aα] |
| 19 | B2 | —H | —C(O)H | —CH$_3$ | —H | [3a(E),3aα] |
| 3 | B2 | —OCH$_3$ | —C(O)H | —CH$_3$ | —H | [3a(E),3aα] |
| 16 | B8 | —OCH$_3$ | —C(O)NHCH$_2$CH$_3$ | —CH$_3$ | —H | [3α(E),3aα] |

TABLE 1-continued
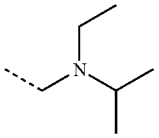
| Co. no. | Exp. no. | —R¹ | ---R² | ---R⁴ | --R⁶ | Phys. data |
|---|---|---|---|---|---|---|
| 24 | B5 | —OCH₃ | 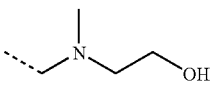 | —CH₃ | —F | [3α(E),3aα] |
| 9 | B5 | —H | 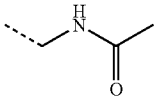 | —CH₃ | —H | [3a(E),3aα] HCl(1:2) |
| 15 | B7 | —H | 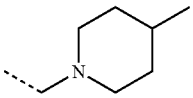 | —CH₃ | —H | [3α(E),3aα] C₂H₂O₄(1:1) |
| 25 | B5 | —OCH₃ | 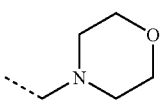 | —CH₃ | —F | [3α(E),3aα] |
| 10 | B5 | —OCH₃ | 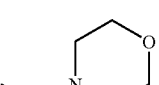 | —CH₃ | —H | [3α(E),3aα] |
| 20 | B5 | —OCH₃ | 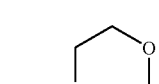 | —CH₃ | —H | A-[3α(E),3aα] |
| 21 | B5 | —OCH₃ | 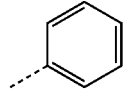 | —CH₃ | —H | B-[3α(E),3aα] |
| 11 | B6 | —H | —CN—OH | —CH₃ | —H | [3α(E),3aα] |
| 12 | B6 | —H | —CN—OCH₃ | —CH₃ | —H | [3α(E),3aα] |
| 13 | B7 | —H | —CN | —CH₃ | —H | [3α(E),3aα] |
| 17 | B9 | —OCH₃ | 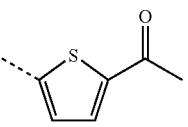 | —CH₃ | —H | [3α(E),3aα] |
| 18 | B9 | —OCH₃ |  | —CH₃ | —H | [3α(E),3aα] |

For a number of compounds, melting points were obtained with a Büchi melting point apparatus B-545. The heating medium is a metal block. The melting of the sample is visually observed by a magnifying lense and a big light contrast. Melting points are measured with a temperature gradient of either 3 or 10 degrees Celsius/minute. The results are summarized in Table 1b.

TABLE 1b

Melting points

| Co. No. | Melting point (° C.) | Visual observation |
|---|---|---|
| 7 | not determinable | foam |
| 9 | 228.6-252.1 | At 228.6° C. shrink, at 239.1° C. black crystals, at 252.1° C. black liquid |
| 13 | 132.2-146.7 | At 132.2° C. shrink, at 146.7° C. light brown sticky liquid |
| 18 | 150.1-171.8 | At 150.1° C. shrink, at 171.8° C. black liquid |
| 20 | 66.5-89.8 | At 66.5° C. shrink, at 89.8° C. light brown sticky liquid |
| 21 | 56.1-68.0 | At 56.1° C. shrink, at 68.0° C. colourless sticky liquid |
| 24 | not determinable | foam |
| 25 | not determinable | foam |

C. Pharmacological Examples

EXAMPLE C1

Binding Experiment for $\alpha_2$-adrenergic Receptor Subtypes and for 5-HT Transporter General The interaction of the compounds according to Formula (I) with h$\alpha_2$-receptors and h5-HT-transporters was assessed in in vitro radioligand binding experiments. In general, a low concentration of a radioligand with a high binding affinity for a particular receptor or transporter is incubated with a sample of a tissue preparation enriched in a particular receptor or transporter or with a preparation of cells expressing cloned human receptors in a buffered medium. During the incubation, the radioligand binds to the receptor or transporter. When equilibrium of binding is reached, the receptor bound radioactivity is separated from the non-bound radioactivity, and the receptor- or transporter-bound activity is counted. The interaction of the test compounds with the receptor is assessed in competition binding experiments. Various concentrations of the test compound are added to the incubation mixture containing the receptor- or transporter preparation and the radioligand. The test compound in proportion to its binding affinity and its concentration inhibits binding of the radioligand. The radioligand used for h$\alpha_{2A}$, h$\alpha_{2B}$ and h$\alpha_{2C}$ receptor binding was [$^3$H]-raulwolscine and for the h5-HT transporter was [$^3$H]paroxetine.

Cell Culture and Membrane Preparation.

CHO cells, stabile transfected with human adrenergic-$\alpha_{2A}$-, —$\alpha_{2B}$ or $\alpha_{2C}$ receptor cDNA, were cultured in Dulbecco's Modified Eagle's Medium (DMEM)/Nutrient mixture Ham's F12 (ratio 1:1)(Gibco, Gent-Belgium) supplemented with 10% heat inactivated fetal calf serum (Life Technologies, Merelbeke-Belgium) and antibiotics (100 IU/ml penicillin G, 100 µg/ml streptomycin sulphate, 110 µg/ml pyruvic acid and 100 µg/ml L-glutamine). One day before collection, cells were induced with 5 mM sodiumbutyrate. Upon 80-90% of confluence, cells were scraped in phosphate buffered saline without $Ca^{2+}$ and $Mg^{2+}$ and collected by centrifugation at 1500×g for 10 min. The cells were homogenised in Tris-HCl 50 mM using an Ultraturrax homogenizer and centrifuged for 10 min at 23,500×g. The pellet was washed once by resuspension and rehomogenization and the final pellet was resuspended in Tris-HCl, divided in 1 ml aliquots and stored at −70° C.

Binding Experiment for $\alpha_2$-adrenergic Receptor Subtypes

Membranes were thawed and re-homogenized in incubation buffer (glycylglycine 25 mM, pH 8.0). In a total volume of 500 µl, 2-10 µg protein was incubated with [$^3$H]raulwolscine (NET-722) (New England Nuclear, USA) (1 nM final concentration) with or without competitor for 60 min at 25° C. followed by rapid filtration over GF/B filter using a Filtermate196 harvester (Packard, Meriden, Conn.). Filters were rinsed extensively with ice-cold rinsing buffer (Tris-HCl 50 mM pH 7.4). Filter-bound radioactivity was determined by scintillation counting in a Topcount (Packard, Meriden, Conn.) and results were expressed as counts per minute (cpm). Non-specific binding was determined in the presence of 1 µM oxymetazoline for h$\alpha_{2A}$- and h$\alpha_{2B}$ receptors and 1 µM spiroxatrine for h$\alpha_{2C}$ receptors.

Binding Experiment for 5-HT Transporter

Human platelet membranes (Oceanix Biosciences Corporation, Hanover, Md., USA) were thawed, diluted in buffer (Tris-HCl 50 mM, 120 mM NaCl and 5 mM KCl) and quickly (max 3 s) homogenised with an Ultraturrax homogenizer. In a total volume of 250 µL, 50-100 µg protein was incubated with [$^3$H]paroxetine (NET-869) (New England Nuclear, USA) (0.5 nM final concentration) with or without competitor for 60 min at 25° C. Incubation was stopped by rapid filtration of the incubation mixture over GF/B filters, prewetted with 0.1% polyethyleneamine, using a Filtermate 196 harvester (Packard, Meriden, Conn.). Filters were rinsed extensively with ice-cold buffer and radioactivity on the filters was counted in a Topcount liquid scintillation counter (Packard, Meriden, Conn.). Data were expressed as cpm. Imipramine (at 1 µM final concentration) was used to determine the non-specific binding.

Data Analysis and Results

Data from assays in the presence of compound were calculated as a percentage of total binding measured in the absence of test compound. Inhibition curves, plotting percent of total binding versus the log value of the concentration of the test compound, were automatically generated, and sigmoidal inhibition curves were fitted using non-linear regression. The $pIC_{50}$ values of test compounds were derived from individual curves.

All compounds according to Formula (I) produced an inhibition at least at the h$\alpha_{2A}$ site (but often also at the h$\neq_{2B}$ and h$\alpha_{2C}$ sites) and simultaneously at the 5-HT transporter site of more than 50% ($pIC_{50}$) at a test concentration ranging between $10^{-6}$ M and $10^{-9}$ M in a concentration-dependent manner. Results are shown in Table 2.

TABLE 2 pIC$_{50}$-values for the h$\alpha_{2A}$, h$\alpha_{2B}$, h$\alpha_{2C}$ and 5-HT transporter receptor site.

| Comp. nr. | pIC$_{50}$ | | | |
|---|---|---|---|---|
| | h$\alpha_{2A}$ | h$\alpha_{2B}$ | h$\alpha_{2C}$ | h5HTT |
| 2 | 8.7 | — | 8.8 | 7.7 |
| 5 | 8.5 | 8.6 | 9.1 | 6.8 |
| 1 | 8.4 | 8.0 | 7.8 | 7.4 |
| 4 | 8.4 | — | 8.8 | 7.0 |
| 7 | 8.4 | — | 8.9 | 7.9 |
| 6 | 8.1 | 8.6 | 9.1 | 7.5 |
| 8 | 7.6 | — | 7.7 | 6.7 |
| 9 | 8.9 | 9.3 | 9.7 | 7.6 |
| 13 | 8.8 | — | 9.3 | 6.9 |
| 16 | 8.5 | — | 8.8 | 6.9 |
| 11 | 8.3 | — | 8.8 | 8.3 |
| 15 | 8.3 | — | 9.1 | 6.6 |
| 10 | 8.2 | 8.4 | 9.5 | 7.6 |
| 12 | 8.2 | — | 8.4 | 7.0 |
| 17 | 7.8 | — | 7.9 | 6.8 |
| 18 | 7.8 | — | 8.0 | 6.6 |
| 19 | 8.3 | — | 9.1 | 6.6 |
| 20 | 6.4 | 7.7 | 7.3 | 7.7 |
| 21 | 7.8 | 8.2 | 8.5 | 8.0 |
| 23 | 7.8 | 8.1 | 8.2 | 7.9 |
| 24 | 7.4 | 7.9 | 8.3 | 8.4 |
| 25 | 8.2 | 8.6 | 9.1 | 7.5 |

The invention claimed is:
1. A compound according to the general Formula (I)

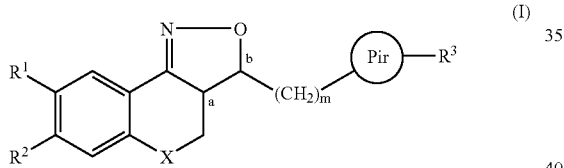

(I)

the pharmaceutically acceptable acid or base addition salts thereof, the stereochemically isomeric forms thereof or the N-oxide form thereof, wherein:

X is CH$_2$, N—R$^7$, S or O;

R$^7$ is selected from the group of hydrogen, alkyl, Ar, Ar-alkyl, alkylcarbonyl, alkyloxycarbonyl and mono- and di(alkyl)aminocarbonyl;

R$^1$ and R$^2$ are each selected from the group of hydrogen, halo, hydroxy, —OSO$_2$H, —OSO$_2$CH$_3$, alkyloxy, alkyloxyalkyloxy, alkyloxyalkyloxyalkyloxy, tetrahydrofuranyloxy, alkylcarbonyloxy, alkyloxyalkylcarbonyloxy, pyridinylcarbonyloxy, alkylcarbonyloxyalkyloxy, alkyloxycarbonyloxy, alkenyloxy, alkenyl-carbonyloxy, mono- or di(alkyl)aminoalkyloxy, —N—R$^{10}$R$^{11}$, alkylthio, Alk and Het, with the proviso that at least one of R$^1$ and R$^2$ selected from the group consisting of Alk and Het, wherein Alk is cyano, CN—OH, CN-oxyalkyl, alkyl, alkyloxyalkyl, alkyloxyalkyloxyalkyl, alkyloxyalkyloxyalkyloxyalkyl, alkylcarbonylalkyl, alkylcarbonyloxyalkyl, alkyloxycarbonylalkyl, Ar-alkyl, Ar-carbonylalkyl, Ar-oxyalkyl, mono- or di(alkyl)aminoalkyl, mono- or di(alkylcarbonyl)aminoalkyl, mono- or di(alkyl)aminocarbonylalkyl, Het-alkyl, formyl, alkylcarbonyl, alkyloxycarbonyl, alkyloxyalkylcarbonyl, mono- or di(alkyl)aminocarbonyl, Ar-carbonyl and Ar-oxycarbonyl;

Ar is phenyl or naphthyl, optionally substituted with one or more halo, cyano, oxo, hydroxy, alkyl, formyl, alkyloxy or amino radicals;

Het is a heterocyclic radical selected from the group consisting of Het$^1$, Het$^2$ and Het$^3$;

Het$^1$ is an aliphatic monocyclic heterocyclic radical selected from the group consisting of pyrrolidinyl, dioxolyl, imidazolidinyl, pyrrazolidinyl, piperidinyl, dioxyl, morpholinyl, dithianyl, thiomorpholinyl, piperazinyl and tetrahydrofuryl;

Het$^2$ is a semi-aromatic monocyclic heterocyclic radical selected from the group consisting of 2H-pyrrolyl, pyrrolinyl, imidazolinyl and pyrrazolinyl;

Het$^3$ is an aromatic monocyclic heterocyclic radical selected from the group consisting of pyrrolyl, pyrazolyl, imidazolyl, furyl, thienyl, oxazolyl, isoxazolyl, thiazolyl, isothiazolyl, pyridinyl, pyrimidinyl, pyrazinyl, pyridazinyl and triazinyl; or an aromatic bicyclic heterocyclic radical selected from the group consisting of quinolinyl, quinoxalinyl, indolyl, benzimidazolyl, benzoxazolyl, benzisoxazolyl, benzothiazolyl, benzisothiazolyl, benzofuranyl and benzothienyl;

wherein each Het$^1$, Het$^2$ and Het$^3$-radical may optionally be substituted on either a carbon or heteroatom with halo, hydroxy, alkyloxy, alkyl, Ar, Ar-alkyl, formyl, alkylcarbonyl or pyridinyl;

R$^{10}$ and R$^{11}$ are each, independently from each other, selected from the group consisting of hydrogen, alkyl, Ar, Ar-alkyl, pyrrolidinylalkyl, piperidinylalkyl, homopiperidinylalkyl, piperazinylalkyl, morpholinylalkyl, mono- or di(alkyl)aminoalkyl, alkylcarbonyl, alkenylcarbonyl, Ar-carbonyl, pyridinylcarbonyl, alkyloxycarbonyl, mono- or di(alkyl)aminocarbonyl, mono- or di(Ar)aminocarbonyl, mono- or di(alkyloxycarbonylalkyl)aminocarbonyl, pyrrolidinylcarbonyl, aminoiminomethyl, alkylaminoiminomethyl, N-benzylpiperazinyliminomethyl, alkylsulphonyl and Ar-sulphonyl ; or R$^{10}$ R$^{11}$ may be taken together and with the N may form a monovalent radical selected from the group of

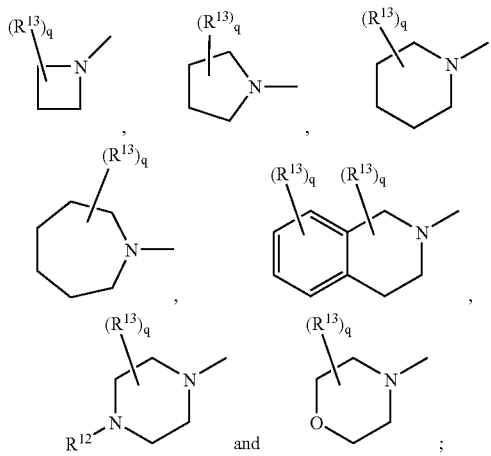

wherein:

$R^{12}$ is selected from the group consisting of hydrogen, alkyl, Ar, Ar-alkyl, Ar-alkenyl, alkylcarbonyl, alkyloxycarbonyl, alkyloxyalkylcarbonyl and mono-or di(alkyl)aminocarbonyl;

each ring being optionally substituted with q radicals $R^{13}$, each radical independently from each other selected from the group of alkyl, oxo, Ar, Ar-alkyl, Ar-alkenyl and alkyloxycarbonyl and q being an integer ranging from 0 to 6 ;or $R^1$ and $R^2$ may be taken together to form a bivalent radical —$R^1$-$R^2$ —selected from the group consisting of —$CH_2$—$CH_2$—$CH_2$—$CH_2$—, —CH═CH—$CH_2$—$CH_2$—, —$CH_2$—$CH_2$—CH═CH—, —$CH_2$—CH═CH—$CH_2$—and —CH═CH—CH═CH;

a and b area symmetric centers;

$(CH_2)m$ is a straight hydrocarbon chain of m carbon atoms, m being an integer ranging from 1 to 4;

Pir is a radical according to any one of Formula (IIa), (IIb) or (IIc)

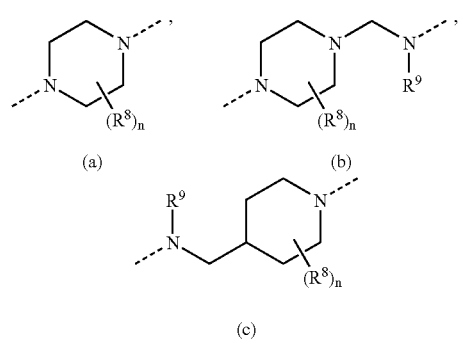

(II)

optionally substituted with n radicals $R^8$, wherein:

each $R^8$ is independently from each other, selected from the group of hydroxy, amino, nitro, cyano, halo and alkyl;

n is an integer ranging from 0 to 5;

$R^9$ is selected from the group consisting of hydrogen, alkyl and formyl;

$R^3$ represents an optionally substituted aromatic homocyclic or heterocyclic ring system together with an optionally substituted and partially or completely hydrogenated hydrocarbon chain of 1 to 6 atoms long with which said ring system is attached to the Pir radical and of which may contain one or more heteroatoms selected from the group of O , N and S;

alkyl represents a straight or branched saturated hydrocarbon radical having from 1 to 6 carbon atoms or a cyclic saturated hydrocarbon radical having from 3 to 6 carbon atoms, optionally substituted with one or more halo, cyano, oxo, hydroxy, formyl or amino radicals;

alkenyl represents a straight or branched unsaturated hydrocarbon radical having one or more double bonds, optionally substituted with one or more halo, cyano, oxo, hydroxy, formyl or amino radicals ; and halo is fluoro, chloro, bromo and iodo.

2. The compound according to claim 1, wherein $R^3$ is a radical according to any one of Formula (IIIa), (IIIb) or (IIIc)

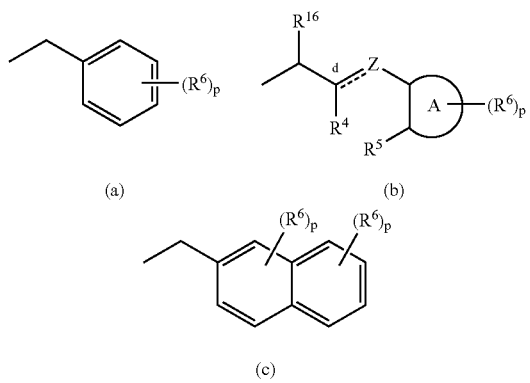

(III)

wherein:

d is a single bond while Z is a bivalent radical selected from the group consisting of —$CH_2$—, —C(═O)—, —CH(OH)—, —C(═N—OH)—, —CH(alkyl)-, —O—, —S—, —S(═O)—, —NH—and —SH—; or d is a double bond while Z is a trivalent radical of formula ═CH— or ═C(alkyl)-;

A is a 5- or 6-membered aromatic homocyclic or heterocyclic ring, selected from the group consisting of phenyl, pyranyl, pyridinyl, pyrazinyl, pyrimidinyl, pyridazinyl, thienyl, isothiazolyl, pyrrolyl, imidazolyl, pyrazolyl, furanyl, oxadiazolyl and isoxazolyl;

p is an integer ranging from 0 to 6;

$R^4$ is alkyl;

$R^5$ is selected from the group consisting of hydrogen, alkyl, Ar, biphenyl, halo and cyano ; or $R^4$ and $R^5$ may be taken together to form a bivalent radical —$R^4$—$R^5$ — selected from the group consisting of —$CH_2$—, ═CH—, —$CH_2$—$CH_2$—, —CH═CH—, —O—, —NH—, ═N—, —S—, —$CH_2$N(-alkyl)-, —N(-alkyl)$CH_2$—, —$CH_2$NH—, —NH$CH_2$—, —CH═N—, —N═CH—, —$CH_2$O— and —O$CH_2$—;

each $R^6$ is independently from each other, selected from the group consisting of hydroxy, amino, nitro, cyano, halo, carboxyl, alkyl, Ar, alkyloxy, Ar-oxy, alkylcarbonyloxy, alkyloxycarbonyl, alkylthio, mono- and di(alkyl)amino, alkylcarbonylamino, mono- and di(alkyl)aminocarbonyl, mono- and di(alkyl)aminocarbonyloxy, mono- and di(alkyl)aminoalkyloxy; or two vicinal radicals $R^6$ may be taken together to form a bivalent radical —$R^6$—$R^6$— selected from the group consisting of —$CH_2$—$CH_2$—O—, —O—$CH_2$—$CH_2$—, —O—$CH_2$—C(═O)—, —C(═O)—$CH_2$—O—, —O—$CH_2$—O—, —$CH_2$—O—$CH_2$—, —O—$CH_2$—$CH_2$—O—, —CH═CH—CH═CH—, —CH═CH—CH═N—, —CH═CH—N═CH—, —CH═N—CH═CH—, —N═CH—CH═CH—, —$CH_2$—$CH_2$—$CH_2$—, —$CH_2$—$CH_2$—C(═O)—, —C(═O)—$CH_2$—$CH_2$—, —$CH_2$—C(═O)—$CH_2$— and —$CH_2$—$CH_2$—$CH_2$—$CH_2$— and $R^{16}$ is selected from the group consisting of hydrogen, alkyl, Ar and Ar-alkyl.

3. The compound according to claim 2, wherein X═O ; m=1; Pir is a radical according to Formula (IIa) wherein n=0; $R^3$ is a radical according to Formula (IIIb) wherein d is a double bond while Z is a trivalent radical of formula ═CH—, A is a phenyl ring, $R^4$ is alkyl, $R^5$ and $R^{16}$ are each hydrogen, $R^6$ is hydrogen or halo and p=1.

4. The compound according to claim 1 wherein at least one of $R^1$ and $R^2$ is selected from the group consisting of cyano optionally substituted with hydroxy or alkyloxy; alkyl ; hydroxyalkyl ; amino alkyl ; alkyloxyalkyl; alkyloxyalkyloxyalkyloxyalkyl ; alkylcarbonyloxyalkyl ; Ar-oxyalkyl ; mono- or di(alkyl)aminoalkyl, the alkyl radicals optionally substituted with hydroxy ; mono- or di(alkylcarbonyl)aminoalkyl ; mono- or di(alkyl)aminocarbonyl ; piperidinylalkyl; morpholinylalkyl ; and thienyl optionally substituted with alkylcarbonyl.

5. The compound according to claim 1 selected from the group consisting of:

- 8-Methoxy-7-methyl-3-[4-(2-methyl-3-phenyl-allyl)-piperazin-1-ylmethyl]-3a,4-dihydro-3H-chromeno[4,3-c]isoxazole;
- {8-Methoxy-3-[4-(2-methyl-3-phenyl-allyl)-piperazin-1-ylmethyl]-3a,4-dihydro-3H-chromeno[4,3-c]isoxazol-7-yl }-methanol;
- 7-Methoxymethyl-3-[4-(2-methyl-3-phenyl-allyl)-piperazin-1-ylmethyl]-3a,4-dihydro-3H-chromeno[4,3-c]isoxazole;
- 8-Methoxy-7-(2-methoxy-ethoxymethoxymethyl)-3-[4-(2-methyl-3-phenyl-allyl)-piperazin-1-ylmethyl]-3a,4-dihydro-3H-chromeno[4,3-c]isoxazole;
- Acetic acid 8-methoxy-3-[4-(2-methyl-3-phenyl-allyl)-piperazin-1-ylmethyl]-3a,4-dihydro-3H-chromeno[4,3-c]isoxazol-7-ylmethyl ester;
- 8-Methoxy-3-[4-(2-methyl-3-phenyl-allyl)-piperazin-1-ylmethyl]-7-phenoxymethyl-3a,4-dihydro-3H-chromeno[4,3-c]isoxazole;
- 2-(Methyl-{3-[4-(2-methyl-3-phenyl-allyl)-piperazin-1-ylmethyl]-3a,4-dihydro-3H-chromeno[4,3-c]isoxazol-7-ylmethyl}-amino)-ethanol;
- 8-Methoxy-3-[4-(2-methyl-3-phenyl-allyl)-piperazin-1-ylmethyl]-7-morpholin-4-ylmethyl-3a,4-dihydro-3H-chromeno[4,3-c]isoxazole;
- 3-[4-(2-Methyl-3-phenyl-allyl)-piperazin-1-ylmethyl]-3a,4-dihydro-3H-chromeno[4,3-c]isoxazole-7-carbaldehyde oxime;
- 3-[4-(2-Methyl-3-phenyl-allyl)-piperazin-1-ylmethyl]-3a,4-dihydro-3H- chromeno[4,3-c]isoxazole-7-carbaldehyde O-methyl-oxime;
- 3-[4-(2-Methyl-3-phenyl-allyl)-piperazin-1-ylmethyl]-3a,4-dihydro-3H-chromeno[4,3-c]isoxazole-7-carbonitrile;
- N-{3-[4-(2-Methyl-3-phenyl-allyl)-piperazin-1-ylmethyl]-3a,4-dihydro-3H-chromeno[4,3-c]isoxazol-7-ylmethyl}-acetamide;
- 8-Methoxy-3-[4-(2-methyl-3-phenyl-allyl)-piperazin-1-ylmethyl]-3a,4-dihydro-3H-chromeno[4,3-c]isoxazole-7-carboxylic acid ethylamide; and
- 1-(5-{8-Methoxy-3-[4-(2-methyl-3-phenyl-allyl)-piperazin-1-ylmethyl]-3a,4-dihydro-3H-chromeno[4,3-c]isoxazol-7-yl}-thiophen-2-yl)-ethanone.

6. A compound which is degraded in vivo to yield a compound according to claim 1.

7. A pharmaceutical composition comprising a pharmaceutically acceptable carrier and, as active ingredient a therapeutically effective amount of a compound according to claim 1.

8. A pharmaceutical composition comprising a pharmaceutically acceptable carrier and, as active ingredient a therapeutically effective amount of a compound according to claim 1 and one or more other compounds selected from the group consisting of antidepressants, anxiolytics and antipsychotics and anti-Parkinson's disease drugs.

* * * * *

UNITED STATES PATENT AND TRADEMARK OFFICE
CERTIFICATE OF CORRECTION

| | | |
|---|---|---|
| PATENT NO. | : 7,465,741 B2 | |
| APPLICATION NO. | : 10/524197 | |
| DATED | : December 16, 2008 | |
| INVENTOR(S) | : Jose Ignacio Andres-Gil et al. | |

It is certified that error appears in the above-identified patent and that said Letters Patent is hereby corrected as shown below:

Column 4,
Line 35, delete "tlivalend" and insert -- trivalent --.
Line 51, delete "-CH-N-," and insert -- -CH=N-, --.

Column 5,
Line 13, delete "=H-," and insert -- =CH-, --.

Column 23,
Line 14, delete "methylbenzeisulfonyloxy" and insert
-- methylbenzenesulfonyloxy --.

Column 29,
Line 35, delete "(0.65 nmol)" and insert -- (0.65 mol) --.

Column 30,
Line 3, delete "eluerit" and insert -- eluent --.
Line 59, delete "TIE" and insert -- THF --.

Column 42,
Line 63, delete "h$\neq_{2B}$" and insert -- ha$_{2B}$ --.

Signed and Sealed this

Eighteenth Day of August, 2009

David J. Kappos
*Director of the United States Patent and Trademark Office*